(12) United States Patent
Bramucci et al.

(10) Patent No.: US 7,560,266 B2
(45) Date of Patent: Jul. 14, 2009

(54) METHOD TO ENHANCE BIODEGRADATION OF SULFONATED ALIPHATIC-AROMATIC CO-POLYESTERS BY ADDITION OF A MICROBIAL CONSORTIUM

(75) Inventors: Michael Bramucci, Boothwyn, PA (US); Vasantha Nagarajan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 274 days.

(21) Appl. No.: 11/347,447

(22) Filed: Feb. 3, 2006

(65) Prior Publication Data
US 2006/0177930 A1     Aug. 10, 2006

Related U.S. Application Data

(60) Provisional application No. 60/650,446, filed on Feb. 4, 2005.

(51) Int. Cl.
| A62D 3/00 | (2007.01) |
| A62D 3/02 | (2007.01) |
| B09B 3/00 | (2006.01) |
| B09C 1/10 | (2006.01) |
| C02F 3/34 | (2006.01) |
| C10G 32/00 | (2006.01) |
| C12N 1/20 | (2006.01) |

(52) U.S. Cl. .............. 435/262.5; 435/252.1; 435/262; 435/282; 435/822

(58) Field of Classification Search ........................ None
See application file for complete search history.

(56) References Cited

U.S. PATENT DOCUMENTS

| 5,171,308 | A | 12/1992 | Gallagher et al. |
| 5,171,309 | A | 12/1992 | Gallagher et al. |
| 5,219,646 | A | 6/1993 | Gallagher et al. |
| 5,295,985 | A | 3/1994 | Rossmesser et al. |
| 5,464,766 | A | 11/1995 | Bruno |
| 5,990,266 | A | 11/1999 | Tadros et al. |
| 6,018,004 | A | 1/2000 | Warzelhan et al. |
| 6,066,494 | A | 5/2000 | Hsich et al. |
| 6,187,569 | B1 | 2/2001 | Bramucci et al. |
| 6,191,176 | B1 | 2/2001 | Tadros et al. |
| 6,254,645 | B1 | 7/2001 | Kellis et al. |
| 6,255,451 | B1 | 7/2001 | Koch et al. |
| 6,297,347 | B1 | 10/2001 | Warzelhan et al. |
| 6,350,607 | B1 | 2/2002 | Cooney, Jr. |
| 6,368,710 | B1 | 4/2002 | Hayes |
| 6,461,840 | B1 | 10/2002 | Bramucci et al. |
| 6,521,717 | B1 | 2/2003 | Itoh |
| 2005/0261465 | A1 | 11/2005 | Nagarajan |

FOREIGN PATENT DOCUMENTS

| DE | 19508737 | 9/1996 |
| EP | 1 090 958 A2 | 4/2001 |

OTHER PUBLICATIONS

PCT International Search Report for International Application No. PCT/US2006/004228 dated Aug. 3, 2006.
Abou-Zeid et al., Degradation of natural and synthetic polyesters under anaerobic conditions. J Biotechnol. 2001;86(2):113-26.
Bramucci et al. Pure bacterial isolates that convert p-xylene to terephthalic acid. Appl Microbiol Biotechnol. 2002;58(2):255-9.
Deshpande MV. Ethanol production from cellulose by coupled saccharification/fermentation using *Saccharomyces cerevisiae* and cellulase complex from *Sclerotium rolfsii* UV-8 mutant. Appl Biochem Biotechnol. 1992;36(3):227-34.
De Wilde et al. Prerequisites for biodegradable plastic materials for acceptance in real-life composting plants and technical aspects. 1998. Polymer Degradation and Stability, 59: 7-12.
Gouda et al. Production of a polyester degrading extracellular hydrolase from *Thermomonospora fusca*. Biotechnol Prog. 2002;18(5):927-34.
Junker, F and Cook, A. Conjugative plasmids and the degradation of arylsulfonates in Comamonas testosteroni. Appl Environ Microbiol. 1997; 63(6):2403-10.
Kint, D. and Munoz-Guerra, S., A review on the potential biodegradability of poly(ethylene terephthalate) Polym Int 1999; 48:346-352.
Kleeburg et al. Biodegradation of aliphatic-aromatic copolyesters by *Thermomonospora fusca* and other thermophilic compost isolates. Appl Environ Microbiol. 1998;64(5):1731-5.
Muller RJ, et al. Biodegradation of polyesters containing aromatic constituents. J Biotechnol. 2001; 86(2):87-95.
Stackebrandt and BM Goebel. Taxonomic note: a place for DNA-DNA reassociation and 16S rRNA sequence analysis in the present species definition in bacteriology. Int J Syst Bacteriol 1994; 44: 846-849.
Witt et al. J. Environ. Polymer. Degrad. 1997; 5(2):81-89.

*Primary Examiner*—David M. Naff
*Assistant Examiner*—Deborah K. Ware

(57) ABSTRACT

A microbial consortium for the biodegradation of sulfonated aliphatic-aromatic co-polyesters having greater than 60 mol percent aromatic acid content based on the total acid content of the co-polyester, created by applying selective pressure. Methods to biodegrade sulfonated aliphatic-aromatic co-polyesters using microbial consortium SPDC-1 are provided.

10 Claims, 1 Drawing Sheet

SEQUENCE LISTING

<160> NUMBER OF SEQ ID NOS: 39

<210> SEQ ID NO 1
<211> LENGTH: 15
<212> TYPE: DNA
<213> ORGANISM: artificial sequence
<220> FEATURE:
<223> OTHER INFORMATION: Primer

<400> SEQUENCE: 1
acgggcggtg tgtac                    15

<210> SEQ ID NO 2
<211> LENGTH: 16
<212> TYPE: DNA
<213> ORGANISM: artificial sequence
<220> FEATURE:
<223> OTHER INFORMATION: Primer

<400> SEQUENCE: 2
gccagcagcc gcggta                                              16

<210> SEQ ID NO 3
<211> LENGTH: 17
<212> TYPE: DNA
<213> ORGANISM: artificial sequence
<220> FEATURE:
<223> OTHER INFORMATION: Primer

<400> SEQUENCE: 3
gttttcccag tcacgac                                             17

<210> SEQ ID NO 4
<211> LENGTH: 17
<212> TYPE: DNA
<213> ORGANISM: artificial sequence
<220> FEATURE:
<223> OTHER INFORMATION: Primer

<400> SEQUENCE: 4
caggaaacag ctatgac                                             17

<210> SEQ ID NO 5
<211> LENGTH: 895
<212> TYPE: DNA
<213> ORGANISM: unknown
<220> FEATURE:
<223> OTHER INFORMATION: Uncultured soil bacterium with closest match to
      GenBank AF507712

<400> SEQUENCE: 5
gccagcagcc gcggtaagac ggagggcgcg agcgttgttc ggaattactg ggcgtaaagc      60
gcgcgcaggc ggacggtgca agtcagggt gaaattctgg ggctcaaccc cggagctgct     120
cttgatactg cctgtctagg gaccggtagg ggccggtgga attcccggtg tagcggtgga    180
atgcgtagag atcgggaaga acacccgtgg cgaaggcggc cggctgggcc ggatccgacg    240
ctgaggcgcg aaagcgtggg gagcaaacag gattagatac cctggtagtc cacgccgtaa    300
acgatgggtg ctagatgccg gggggagcga ccctttcggt gtcgtagcta acgcgttaag    360
caccccgcct gggagtacg gccgcaaggc tgaaactcaa aggaattgac ggggccccgc     420
acaagcggtg gagcatgtgg tttaattcga agcaacgcga agaaccttac ctgggcttga    480
catgcacgtg aaaggctctg gaaacagggg ccctccttcg ggacacgtgc acaggtgctg    540
catggctgtc gtcagctcgt gtcgtgagat gttgggttaa gtcccgcaac gagcgcaacc    600
cctgccccgt gttgctaacg ggtaaagccg aggactctcg ggggactgcc ggcgccaagc    660
cggaggaagg tggggatgat gtcaagtcat catggccctt acgcccaggg cgacacacgt    720
gctacaatgg ccggtacaga gggctgcgaa cccgtgaggg ggagcgaatc ccagaaagcc    780
ggtctaagtt cggattgcag tctgcaactc gactgcatga agccggaatc gctagtaatc    840
gcggatcagc catgccgcgg tgaatacgtt cccgggcctt gtacacaccg cccgt         895

<210> SEQ ID NO 6

<211> LENGTH: 892
<212> TYPE: DNA
<213> ORGANISM: unknown
<220> FEATURE:
<223> OTHER INFORMATION: Bacterium with closest match to GenBank
      AF227859

<400> SEQUENCE: 6

```
acgggcggtg tgtacaagac ccgggaacgt attcaccgcg gcatgctgat ccgcgattac      60
tagcaattcc ggcttcatgc aggcgagttg cagcctgcaa tccgaactga gaccggcttt     120
ttgggattgg ctccggatcg ctccttcgcg gcccttttgta ccggccattg tagcacgtgt    180
gtagcccagg tcataagggg catgatgatt tgacgtcatc cccgccttcc tccggtttgt    240
caccggcagt cagcctagag tgcccacccc aggtgctggc aactaagctc aagggttgcg    300
ctcgttgcgg gacttaaccc aacatctcac gacacgagct gacgacaacc atgcaccacc    360
tgtctcccct gtcccgaaag gcctgcccc atctctggaa cattcagggg gatgtcaaga    420
cctggtaagg ttcttcgcgt tgcttcgaat taaaccacat gctccactgc ttgtgcgggt    480
ccccgtcaat tcctttgagt ttcagccttg cggccgtact cccaggcgg agtgcttaat    540
gtgttaactt cggcaccgaa aggttagtcc cctccgacac ctagcactca tcgtttacgg    600
cgtggactac cagggtatct aatcctgttt gctccccacg cttcgcgcc tcagcgtcag    660
ttacagccca gaaagccgcc ttcgccactg gtgttcctcc atatctctac gcatttcacc    720
gctacacatg gaattccgct tccctctgct gcactcaagt cctccagttt ccagtgcgca    780
gcagggttga gccccgctct tatacaccag acttaaagga ccgcctgcgc gcgctttacg    840
cccaataatt ccggacaacg ctcgccccct acgtattacc gcggctgctg gc            892
```

<210> SEQ ID NO 7
<211> LENGTH: 897
<212> TYPE: DNA
<213> ORGANISM: Xanthomonas sp.

<400> SEQUENCE: 7

```
acgggcggtg tgtacaaggc ccgggaacgt attcaccgca gcaatgctga tctgcgatta      60
ctagcgattc cgacttcatg gagtcgagtt gcagactcca atccggactg agagaaggtt    120
tctgggattg gctcccccte gcgggttcgc agccctctgt ccttcccatt gtagtacgtg    180
tgtagccctg gccgtaaggg ccatgatgac ttgacgtcat ccccaccttc ctccggtttg    240
tcaccggcag tctccttaga gttcccacca ttacgtgctg gcaactaagg acaagggttg    300
cgctcgttgc gggacttaac ccaacatctc acgacacgag ctgacgacag ccatgcagca    360
cctgtctcag ggtcccgaa ggcacccccg catctctgca gggttccctg gatgtcaagg    420
ccaggttaag gttcttcgcg ttgcatcgaa ttaaaccaca tactccaccg ctttgtgcgg    480
gccccccgtc aattcctttg agtttcagtc ttgcgaccgt actccccagg cggcgaactt    540
aacgcgttta gcttcgatac tgagttcccg attgaaccca acatccagtt cgcatcgttt    600
agggcgtgga ctaccagggt atctaatcct gtttgctccc cacgctttcg tgcctcagtg    660
tcagtactgg tccaggcagt cgccttcgcc acgggtgttc ctcctgatct ctacgcattt    720
cactgctaca ccaggaattc cactgccctc taccgcgctc tagcccgcca gtatccaatg    780
cagttcccag gttgagccca gggctttcac atcagactta gcgaaccacc tacgcacgct    840
ttacgcccag taattccgag taacgcttgc accttcgta ttaccgcggc tgctggc        897
```

<210> SEQ ID NO 8

<211> LENGTH: 899
<212> TYPE: DNA
<213> ORGANISM: Thermoanaerobacter wiegelii

<400> SEQUENCE: 8

| | | | | | |
|---|---|---|---|---|---|
| acgggcggtg | tgtacaaggc | ccgggaacgt | attcaccgcg | gcatggctga | tccgcgatta | 60 |
| ctagcgattc | cggcttcatg | cagtcgagtt | gcagactgca | atccgaactt | agaccggctt | 120 |
| tctgggattc | gctcccccctc | acgggttcgc | agccctctgt | accggccatt | gtagcacgtg | 180 |
| tgtcgccctg | ggcgtaaggg | ccatgatgac | ttgacatcat | ccccaccttc | ctccggcttg | 240 |
| gcgccggcag | tcccccgcga | gtgctcggct | cgcccgttag | caacacgggg | caggggttgc | 300 |
| gctcgttgcg | ggacttaacc | caacacctca | cggcacgagc | tgacgacaac | catgcaccac | 360 |
| ctgtgccggc | tccggcccc | aaggccgggt | cggtcgcctt | tcggctccct | acctccggca | 420 |
| tgtcaagccc | tggtaaggtt | cttcggttag | catcgaatta | aaccacatgc | tccaccgctt | 480 |
| gtgcgggccc | ccgtcaattc | ctttgagttt | caaccttgcg | gccgtactcc | ccaggcgggg | 540 |
| tgcttaatgc | gttagctgcg | gcacggaggg | cctacacccc | ccacacctag | cacccatcgt | 600 |
| ttacggctgg | gactaccagg | gtatctaatc | ctgtttgctc | cccagctttt | cgtgcctcag | 660 |
| cgtcagggac | cgtccaggta | gccgccttcg | ccactggtgt | tcctcccgat | ctctacgcat | 720 |
| ttcaccgcta | caccgggaat | tccactaccc | tctccgccc | tcaagaccgc | cagtctcctg | 780 |
| agcccttccc | cggttgagcc | gggggctttc | acccaggact | taacggcccg | cctacgcacc | 840 |
| ctttacgccc | agtgattccg | ggcaacgctc | gccccctacg | tgttaccgcg | gctgctggc | 899 |

<210> SEQ ID NO 9
<211> LENGTH: 890
<212> TYPE: DNA
<213> ORGANISM: Amycolatopsis sacchari

<400> SEQUENCE: 9

| | | | | | |
|---|---|---|---|---|---|
| gccagcagcc | gcggtaatac | gtaggggcg | agcgttgtcc | ggaattattg | ggcgtaaaga | 60 |
| gctcgtaggc | ggtttgtcgc | gtctgccgtg | aaaaccgggg | gcttaactct | cggcttgcgg | 120 |
| tggatacggg | cagactagag | tgcggtaggg | gagactggaa | ttcctggtgt | agcggtgaaa | 180 |
| tgcgcagata | tcaggaggaa | caccggtggc | gaaggcgggt | ctctgggccg | ctactgacgc | 240 |
| tgaggagcga | aagcgtgggg | agcgaacagg | attagatacc | ctggtagtcc | acgccgtaaa | 300 |
| cgttgggcgc | taggtgtggg | tggcgttttt | gttgtccgtg | ccgtagctaa | cgcattaagc | 360 |
| gccccgcctg | gggagtacgg | ccgcaaggct | aaaactcaaa | ggaattgacg | ggggcccgca | 420 |
| caagcggcgg | agcatgtgga | ttaattcgat | gcaacgcgaa | gaaccttacc | tgggcttgac | 480 |
| atacaccgga | ccgctccaga | gatggggctt | ccctttgtgg | ctggtgtaca | ggtggtgcat | 540 |
| ggctgtcgtc | agctcgtgtc | gtgagatgtt | gggttaagtc | ccgcaacgag | cgcaacccct | 600 |
| gccccgtgtt | gctaccggga | aagccgagca | ctcgcgggg | actgccggcg | acaagccgga | 660 |
| ggaaggcggg | gatgacgtca | aatcatcatg | ccctggatgc | cctgggctac | acacatgcta | 720 |
| caatggccga | tacagcgggt | tgcgaccccg | tgaggggaag | ccaatccctt | aaagccggcc | 780 |
| tcagttcgga | tcgcaggctg | caactcgcct | gcgtgaaggc | ggaatcgcta | gtaatcgccg | 840 |
| gtcagcaaac | ggcggtgaat | acgttcccgg | gccttgtaca | caccgccgt | 890 |

<210> SEQ ID NO 10
<211> LENGTH: 892
<212> TYPE: DNA
<213> ORGANISM: Rhizobiaceae strain -continued

<400> SEQUENCE: 10

| acgggcggtg | tgtacaaggc | ccgggaacgt | attcaccgca | gcatgctgat | ctgcgattac | 60 |
| tagcgattcc | gccttcatgc | actcgagttg | cagagtgcaa | tctgaactga | gacggctttt | 120 |
| ggggattagc | tccaggtcgc | cctttcgctg | cccattgtca | ccgccattgt | agcacgtgtg | 180 |
| tagcccagcc | cgtaagggcc | atgaggactt | gacgtcatcc | ccaccttcct | ctcggcttat | 240 |
| caccggcagt | cccctaaag | tgcccaactt | aatgatggca | actaggggcg | agggttgcgc | 300 |
| tcgttgcggg | acttaaccca | acatctcacg | acacgagctg | acgacagcca | tgcagcacct | 360 |
| gtgttcgcgc | cagccgaact | gaaggaagcc | atctctggca | tccatacgcg | acatgtcaag | 420 |
| ggctggtaag | gttctgcgcg | ttgcttcgaa | ttaaaccaca | tgctccaccg | cttgtgcggg | 480 |
| cccccgtcaa | ttcctttgag | ttttaatctt | gcgaccgtac | tccccaggcg | ggatgcttaa | 540 |
| agcgttagct | gcgccactga | acagcaagct | gcccaacggc | tagcatccat | cgtttacggc | 600 |
| gtggactacc | agggtatcta | atcctgtttg | ctccccacgc | tttcgcgcct | cagcgtcaga | 660 |
| accggaccag | taagccgcct | tcgccactgg | tgttcttgcg | aatatctacg | aatttcacct | 720 |
| ctacactcgc | agttccactt | acctcttccg | gtctcgagac | atccagtatc | aaaggcaatt | 780 |
| ccgaggttga | gccccgggat | ttcacccctg | acttaaacgt | ccgcctacgc | gccctttacg | 840 |
| cccagtgatt | ccgagcaacg | ctagccccct | tcgtattacc | gcggctgctg | gc | 892 |

<210> SEQ ID NO 11
<211> LENGTH: 885
<212> TYPE: DNA
<213> ORGANISM: Pigmentiphaga sp.

<400> SEQUENCE: 11

| gccagcagcc | gcggtaatac | gtagggtgca | agcgttaatc | ggaattactg | ggcgtaaagc | 60 |
| gtgcgcaggc | ggttcggaaa | gaaagatgtg | aaatcccagg | gctcaacctt | ggaactgcat | 120 |
| ttttaactcc | cgaactagag | tgtgtcagag | ggaggtggaa | ttccacgtgt | agcagtgaaa | 180 |
| tgcgtagata | tgtggaggaa | caccgatggc | gaaggcagcc | tcctgggata | acactgacgc | 240 |
| tcatgcacga | aagcgtgggg | agcaaacagg | attagatacc | ctggtagtcc | acgccctaaa | 300 |
| cgatgtcaac | tagctgttgg | gttcttcgga | gcttggtagc | gcagctaacg | cgtgaagttg | 360 |
| accgcctggg | gagtacggtc | gcaagattaa | aactcaaagg | aattgacggg | acccgcaca | 420 |
| agcggtggat | gatgtggatt | aattcgatgc | aacgcgaaaa | accttaccta | cccttgacat | 480 |
| gtccggaatc | ccgaagagat | ttgggagtgc | tcgaaagaga | accggaacac | aggtgctgca | 540 |
| tggccgtcgt | cagctcgtgt | cgtgagatgt | tgggttaagt | cccgcaacga | gcgcaaccct | 600 |
| tgtcattagt | tgctacgaaa | gggcactcta | atgagactgc | cggtgacaaa | ccggaggaag | 660 |
| gtggggatga | cgtcaggtcc | tcatggccct | tatgggtagg | gcttcacacg | tcatacaatg | 720 |
| gtcgggacag | agggctgcca | acccgcgagg | gggagctaat | cccagaaacc | cgatcgtagt | 780 |
| ccggattgca | gtctgcaact | cgactgcatg | aagtcggaat | cgctagtaat | cgcggatcag | 840 |
| catgtcgcgg | tgaatacgtt | cccgggtctt | gtacacaccg | cccgt | | 885 |

<210> SEQ ID NO 12
<211> LENGTH: 694
<212> TYPE: DNA
<213> ORGANISM: Desulfotomaculum geothermicum

<400> SEQUENCE: 12

| | |
|---|---|
| gccagcagcc gcggtaatac gtaggggggcg agcgttgtcc ggaatcactg ggcgtaaagg | 60 |
| gagcgtaggc ggccttgtgt gtcctgcgtg aaaggcgccg gcttaaccgg cgaaggtcgt | 120 |
| gggaaactgc agggcttgag tgccggagag ggtggcggaa ttcccggtgt agcggtgaaa | 180 |
| tgcgtagata tcgggaggaa caccagtggc gaaggcggcc acctgacgg taactgacgc | 240 |
| tgaggctcga agctggggg agcaaacagg attagatacc ctggtagtcc cagccgtaaa | 300 |
| cgatgggtgc taggtgttgt gggctttgag cctgctgtgc cgtaggacac ccaataagca | 360 |
| ccccgcctgg ggagtacggc cgcaaggctg aaactcaaag gaattgacgg gggcccgcac | 420 |
| aagcggtgga gcatgtggtt taattcgaag caacgcgaag aaccttacca ggccttgaca | 480 |
| tcgcccggaa agccatggaa acatggccct cctttggac cgggtgacag gtggtgcatg | 540 |
| gtcgtcgtca gctcgtgtcg tgagatgttg ggttaagtcc cgcaacgagc gcaaccctcg | 600 |
| cccttagttg ccaacaccgt gggtgggcac tctaagggga ctgccggtga caaaccggag | 660 |
| gaaggtgggg atgaggtcag atcatcatgc ccct | 694 |

<210> SEQ ID NO 13
<211> LENGTH: 893
<212> TYPE: DNA
<213> ORGANISM: unknown
<220> FEATURE:
<223> OTHER INFORMATION: Uncultured bacterium with closest match to
      GenBank AY193179

<400> SEQUENCE: 13

| | |
|---|---|
| acgggcggtg tgtacaaggc ccgggaacgt attcaccgcg gcgttctgat ccgcgattac | 60 |
| tagcgattcc ggcttcacga aggcgagttg cagccttcga tccgaactgg gaccggtttt | 120 |
| agggattcgc tccccctcgc ggggtggcag cccattgtac cggccattgt agcacgtgtg | 180 |
| tagccctggg cataagggcc atgatgattt gacgtcatcc ccaccttcct ccggtttgtc | 240 |
| accggcagtt ccccgtgagt ccccagccga actgatggcg acacggggca ggggttgcgc | 300 |
| tcgttgcggg acttaaccca acatctcacg acacgagctg acgacaacca tgcagcacct | 360 |
| gtgccggctc cccgaagggt cggccaccct ttcgggcgcc taccaccggc atgtcaagcc | 420 |
| caggtaaggt tcttcgcgtt gcttcgaatt aaaccacatg ctccaccgct tgtgcgggcc | 480 |
| cccgtcaatt cctttgagtt tcagccttgc ggccgtactc cccaggcgga gtgcttaatg | 540 |
| tgttagctac ggcacggaca acaaaaacgc cacccacacc tagcgcccaa cgtttacggc | 600 |
| gtggactacc agggtatcta atcctgtttg ctccccacgc tttcgcgcct cagcgtcgga | 660 |
| tccggcccag ccggccgcct tcgccacggg tgttcttccc gatctctacg cattccaccg | 720 |
| ctacaccggg aattccaccg gcccctaccg gtccctagac aggcagtatc aagagcagct | 780 |
| ccggggttga gccccagaat tcaccccctg acttgcaccg tccgcctgcg cgcgctttac | 840 |
| gcccagtaat tccgaacaac gctcgcgccc tccgtcttac cgcggctgct ggc | 893 |

<210> SEQ ID NO 14
<211> LENGTH: 892
<212> TYPE: DNA
<213> ORGANISM: unknown
<220> FEATURE:
<223> OTHER INFORMATION: Uncultured soil bacterium with closest match to
      GenBank AY493977

<400> SEQUENCE: 14

| | |
|---|---|
| gccagcagcc gcggtaacac gtaggggggcg agcgttgccc ggaatcactg ggcgtaaagg | 60 |
| gtgcgtaggc gggccgttaa gtcctgggtg aaagtccccg gctcaaccgg gggagggctc | 120 |

-continued

```
aggagactgg cggtcttgag ggccggagag ggtagtggaa ttcccggtgt agcggtgaaa    180
tgcgtagaga tcgggaggaa cacccgtggc gaaggcggct acctggacgg tacctgacgc    240
tgaggcacga aagctggggg agcaaacagg attagatacc ctggtagtcc cagccgtaaa    300
cgatgggtgc taggtgtggg gggtgtaggc cctccgtgcc gcagctaacg cattaagcac    360
cccgcctggg gagtacggcc gcaaggttga aactcaaagg aattgacggg gcccgcaca     420 agcggtggag catgtggttt aattcgatgc taaccgaaga accttaccag gcttgacat     480 gcacgtgaaa gcctctggaa acaggggccc tccttcggga cacgtgcaca ggtgctgcat    540
ggctgtcgtc agctcgtgtc gtgagatgtt gggttaagtc ccgcaacgag cgcaacccct    600
gccccgtgtt gctaacgggt aaagccgagg actctcgggg gactgccggc gccaagccgg    660
aggaaggtgg ggatgatgtc aagtcatcat ggcccttacg cccagggcga cacacgtgct    720
acaatggccg gtacagaggg ctgcgaaccc gtgaggggga gcgaatccca gaaagccggt    780
ctaagttcgg attgcagtct gcaactcgac tgcatgaagc cggaatcgct agtaatcgcg    840
gatcagccat gccgcggtga atacgttccc gggccttgta cacaccgccc gt           892
```

<210> SEQ ID NO 15
<211> LENGTH: 889
<212> TYPE: DNA
<213> ORGANISM: Bacillus mucilaginosus

<400> SEQUENCE: 15

```
gccagcagcc gcggtaatac gtaggggggcg agcgttgtcc ggaattattg ggcgtaaagc     60
gcgcgcaggc ggtcctttaa gtctggtgta taagagcggg gctcaaccct gctgcgcact    120
ggaaactgga ggacttgagt gcagcagagg gaagcggaat ccatgtgta gcggtgaaat     180 gcgtagagat atggaggaac accagtggcg aaggcggctt tctgggctgt aactgacgct    240
gaggcgcgaa agcgtgggga gcaaacagga ttagataccc tggtagtcca cgccgtaaac    300
gatgagtgct aggtgtcgga ggggactaac ctttcggtgc cgaagttaac acattaagca    360
ctccgcctgg ggagtacggc cgcaaggctg aaactcaaag gaattgacgg ggacccgcac    420
aagcggtgga gcatgtggtt taattcgaag caacgcgaag aaccttacca ggccttgaca    480
tcgcccggaa agccatggaa acatggcccc cttttggac cgggtgacag gtggtgcatg    540
gtcgtcgtca gctcgtgtcg tgagatgttg ggttaagtcc cgcaacgagc gcaaccctgt    600
agcttagttg ccagcacctg gggtgggcac tctaggctga ctgccggtga caaaccggag    660
gaaggcgggg atgacgtcaa atcatcatgc cccttatgac ctgggctaca cacgtgctac    720
aatggccggt acaaagggcc gcgaaggagc gatccggagc caatcccaaa aagccggtct    780
cagttcggat tgcaggctgc aactcgcctg catgaagccg gaattgctag taatcgcgga    840
tcagcatgcc gcggtgaata cgttcccggg tcttgtacac accgcccgt               889
```

<210> SEQ ID NO 16
<211> LENGTH: 889
<212> TYPE: DNA
<213> ORGANISM: Chromobacterium violaceum

<400> SEQUENCE: 16

```
gccagcagcc gcggtaatac gtagggtgca agcgttaatc ggaattactg ggcgtaaagc     60
gtgcgcaggc ggttcggaaa gaaagatgtg aaatcccagg gctcaacctt ggaactgcat    120
ttttaactcc cgaactagag tgtgtcagag ggaggtggaa ttccacgtgt agcagtgaaa    180
```

```
tgcgtagata tgtggaggaa caccgatggc gaaggcagcc tcctgggata cactgacgc      240 tcatgcacga aagcgtgggg agcaaacagg attagatacc ctggtagtcc acgccctaaa    300
cgatgtcaac tagctgttgg gttcttcgga gcttggtagc gcagctaacg cgtgaagttg    360
accgcctggg gagtacggtc gcaagattaa aactcaaagg aattgacggg ggcccgcaca    420
agcggtggag catgtggttt aattcgacgc aacgcgaaga accttaccag cccttgacat    480
gcccggatgg tttccagaga tggattcctc ccagcaatgg gccgggacac aggtgctgca    540
tggctgtcgt cagctcgtgt cgtgagatgt tgggttaagt cccgcaacga gcgcaaccct    600
cgccactagt tgccatcatt aagttgggca ctcagtggg actgccggtg ataagccgga    660
ggaaggtggg gatgacgtca agtcatcatg gcccttatgg gctgggctac acacgtgcta    720
caatggcggt gacaatgggc agccacccag cgatggggag ctaatcccaa aaagccgtct    780
cagttcggat tgcactctgc aactcgagtg catgaagtcg gaatcgctag taatcgcgga    840
tcagcatgcc gcggtgaata cgttcccggg ccttgtacac accgcccgt                889

<210> SEQ ID NO 17
<211> LENGTH: 889
<212> TYPE: DNA
<213> ORGANISM: Hyphomicrobium sp.

<400> SEQUENCE: 17
gccagcagcc gcggtaatac gaaggggggct agcgttgttc ggaatcactg ggcgtaaagc     60
gcacgtaggc ggatttgcca gtcagggggtg aaatcccggg gctcaacctc ggaactgcct   120
ctgatacagc aagtctagag tccgggagag gtgagtggaa ttcctagtgt agaggtgaaa    180
ttcgtagata ttaggaggaa caccagtggc gaaggcggct cactggtccg gcactgacgc    240
tgaggtgcga aagcgtgggg agcaaacagg attagatacc ctggtagtcc acgccgtaaa    300
cgatggatgc tagccgttgg caagcttgct tgtcagtggc gcagctaacg cattaagcat    360
cccgcctggg gagtacggcc gcaaggttaa aactcaaagg aattgacggg ggcccgcaca    420
agcggtggag catgtggttt aattcgacgc aacgcgaaga accttaccag cccttgacat    480
gcccggacgg tttccagaga tggattcctc ccagcaatgg gccgggacac aggtgctgca    540
tggctgtcgt cagctcgtgt cgtgagatgt tgggttaagt cccgcaacga gcgcaaccct    600
cgccattagt tgccatcatt aagttgggca ctcagtggg actgccggtg ataagccgga    660
ggaaggtggg gatgacgtca agtcatcatg gcccttatgg gctgggctac acacgtgcta    720
caatggcggt gacaatgggc agccactcag cgatgaggag ctaatcccta aaagccgtct    780
cagttcggat tgagctctgc aactcgagct catgaagtcg gaatcgctag taatcgcgga    840
tcagcatgcc gcggtgaata cgttcccggg ccttgtacac accgcccgt                889

<210> SEQ ID NO 18
<211> LENGTH: 892
<212> TYPE: DNA
<213> ORGANISM: unknown
<220> FEATURE:
<223> OTHER INFORMATION: Uncultured earthworm intestine bacterium with
      closest match to GenBank AY154482

<400> SEQUENCE: 18
acgggcggtg tgtacaagac ccgggaacgt attcaccgca gcgttgctga tctgcgatta     60
ctagcgattc cagcttcatg gagtcgagtt gcagactcca atccgaactg aggacggttt   120
tagcgattag ctccccctcg cgggattgcg acgttttgta ccgtccattg tagcacgtgt   180
```

```
gtagccctga gcataaaggc catgatgact tgacatcatc cccaccttcc tccgttttat    240
caacggcagt ctcaacagag tgcccaactt aatgatggca actgttgata agggttgcgc    300
tcgttgcggg acttaaccca acatctcacg cacgagctg acgacagcca tgcagcacct     360
tgtttcgggt ccggtttccc ggactgtcgg cgttacccga cattccctca cattctagcc    420
caggtaaggt tcttcgcgtt gcgtcgaatt aaaccacatg ctccaccgct tgtgcgggtc    480
cccgtcaatt cctttgagtt tcactcttgc gagcgtactc cccaggcgga atacttaaaa    540
cgttagcgac ggcacccgga gcattgaaac tccagacacc aagtattcat cgtttagggc    600
caggactacc ggggtatcta atcccgtttg ctcccctggc tttcgcgcat cagcgtcagt    660
gtcggcccag caacccgcct tcgcctcagg tgttcctctt gatatctacg catttcaccg    720
ctacaccaag aattccggtt gcctcttccg cactctagca cagcagtatc acttggccgt    780
tctgagttaa gctcagagat ttcacaagtg acttaccgcg ccgcctgcgc gccctttacg    840
cccagtaaat ccgaacaacg cttgctccct acgtattacc gcggctgctg gc            892

<210> SEQ ID NO 19
<211> LENGTH: 893
<212> TYPE: DNA
<213> ORGANISM: unknown
<220> FEATURE:
<223> OTHER INFORMATION: Uncultured bacterium with closest match to
      GenBank AY186075

<400> SEQUENCE: 19
acgggcggtg tgtacaaggc ccgggaacgt attcaccgca gtatgctgac ctgcgattac     60
tagcgattcc gccttcatgc aggcgagttg cagcctgcaa tccgaactga gaccggcttt    120
ctcggattcg ctccccctcg cgggttcgct tccgtctgta ccggccattg tagcacgtgt    180
gtcgcccagg gcataagggg catgatggtt tgacgtcgtc ccccaccttc ctccggtttg    240
tcaccggcag tccgctgtga gtccccaccc caggtgctgg caaacagcg taggggttgc     300 gctcgttgcg ggacttaacc caacatctca cgacacgagc tgacgacaac catgcaccac    360
ctgtctccgc gctccccgaa gggcaccccc gtgtttccac ggggtcgcg ggatgtcaag     420 ccctggtaag gttcttcgcg ttgcatcgaa ttaaaccaca tgctccaccg cttgtgcggg    480
cccccgtcaa ttcctttgag tttcagtctt gcgaccgtac tccccaggcg gcgaacttaa    540
cgcgttagct tcgatactga gttcccgatt gaacccaaca tccagttcgc atcgtttagg    600
gcgtggacta ccagggtatc taatcctgtt tgctccccac gctttcgtgc ctcagtgtca    660
gtactggtcc aggcagtcgc cttcgccacg ggtgttcctc ctgatctcta cgcatttcac    720
tgctacacca ggaattccac tgccctctgc cgcactctag cccgccagta tccaatgcag    780
ttcccaggtt gagcccaggg ctttcacatc agacttagcg aaccacctac gcacgcttta    840
cgcccagtaa ttccgagtaa cgcttgcacc cttcgtatta ccgcggctgc tgg           893

<210> SEQ ID NO 20
<211> LENGTH: 889
<212> TYPE: DNA
<213> ORGANISM: Anoxybacillus toebii

<400> SEQUENCE: 20
gccagcagcc gcggtaatac gtaggggggcg agcgttgtcc ggaatcactg ggcgtaaagg     60
gagcgtaggc ggccctgtaa gtcctgcgtg aaaggcgccg gctcaaccgg cgacagtcgt    120
gggaaactgc ggggcttgag tgccggagag ggtggcggaa ttcccggtgt agcggtgaaa    180
```

```
tgcgtagata tcgggaggaa caccagtggc gaaggcggcc acctggacgg tgactgacgc      240
tgaggctcga aagctggggg agcaaacagg attagatacc ctggtagtcc cagccgtaaa      300
cgatgggtgc taggtgttgt gggccttgag cctgctgtgc cgtaggtcac ccaataagca      360
ccccgcctgg ggagtacggc cgcaaggctg aaactcaaag gaattgacgg gggcccgcac      420
aagcggtgga gcatgtggtt taattcgaag ctacgcgaag aaccttacca ggccttgaca      480
tcacccggaa agccatggaa acatggccct ccttcgggac cgggtgacag gtggtgcatg      540
gtcgtcgtca gctcgtgtcg tgagatgttg ggttaagtcc cgcaacgagc gcaaccctcg      600
cccttagttg ccagcacttc gggtgggcac tctaagggga ctgccggtga caaaccggag      660
gaaggtgggg atgacgtcag atcatcatgc cccttatggc ctgggctaca cacgtgctac      720
aatggccggt acaaacggaa gcgaaggggc gacccgagc gaatccgaaa aagccggtct      780
cagttcggat cgcaggctgc aactcgcctg cgtgaaggcg aatcgctag taatcgcggg       840 tcagcatacc gcggtgaata cgttcccggg ccttgtacac accgcccgt                  889

<210> SEQ ID NO 21
<211> LENGTH: 892
<212> TYPE: DNA
<213> ORGANISM: Sphaerobacter thermophilus

<400> SEQUENCE: 21
acgggcggtg tgtacaagac ccgggaacgt attcaccgcg gcatgctgat ccgcgattac       60
tagcaattcc ggcttcatgc aggcgagttg cagcctgcaa tccgaactga gaccggcttt      120
ttgggattag ctccggatcg ctccttcgca acccgttgta ccggccattg tagcacgtgt      180
gtagccccgg gcataagggc catgatgatt tgacgtcatc cccaccttcc tccggttgt       240 caccggcagt ctcccgtgag tcccctccct gggctggta acacgggacg agggttgcgc       300
tcgttgcggg acttaaccca acatctcacg acacgagctg acgacagcca tgcagcacct      360
gtctcccggc tccccgaagg gcacccccg gtttcccagg ggttccgggg atgtcaagcc       420
ctggtaaggt tctgcgcgtt gcgtcgaatt aaaccacacg ctccgctgct tgtgcgggcc      480
cccgtcaatt cctttgagtt ttagccttgc ggccgtactc cccaggcggt ggacttactg      540
cgttagcgcc ggcacggaag gggtcaacac ctcccacacc tagtccacag cgttactgc      600 gcggactacc ggggtatcta atcccgttcg ctccccgcgc cttcgcgcct cagcgtcagg      660
tcagggccag ctggccgcct tcgccaccgg tgttcctccc gatctctacg catttcaccg      720
ctacaccggg aattccacca gcctctccct gcctctagcc accccgtctc gcacgaccct      780
ccccggttga gccgggggct ttcacgtgcg acgcgggcag ccgcctacgc gccctttacg      840
cccagtaact ccggacaacg ctcgcaccct acgtcttacc gcggctgctg gc              892

<210> SEQ ID NO 22
<211> LENGTH: 891
<212> TYPE: DNA
<213> ORGANISM: Paenibacillus sp.

<400> SEQUENCE: 22
gccagcagcc gcggtaagac ggagggcgcg agcgttgttc ggaattactg ggcgtaaagc       60
gcgcgcaggc ggacggtgca agtcaggggt gaaattctgg ggctcaaccc cggagctgct      120
cttgatactg cctgtctagg accggtagg ggccggtgga attcccggtg tagcggtgga       180
atgcgtagag atcaggagga acaccgatgg cgaaggcagc tctctggcct gtaactgacg      240
ctgaggcgcg aaagcgtggg gagcaaacag gattagatac cctggtagtc cacgccgtaa      300
```

```
acgatgagtg ctaggtgtta gaggttttga acctttagtg ccgaagttaa cacattaagc    360
actccgcctg gggagtacgg tcgcaagact gaaactcaaa ggaattgacg ggggcccgca    420
caagcggtgg agcatgtggt ttaattcgaa gcaacgcgaa gaaccttacc agggcttgac    480
atccctctga ccctcctaga gataggagct cccttcgggg cagaggtgac aggtggtgca    540
tggttgtcgt cagctcgtgt cgtgagatgt tgggttaagt cccgcaacga gcgcaaccct    600
tgtccttagt tgccagcact tggggtgggc actctaggct gactgccggt gacaaaccgg    660
aggaaggcgg ggatgacgtc aaatcatcat gccccttatg acctgggcta cacacgtgct    720
acaatggccg gtacaaaggg ccgcgaagga gcgatccgga gccaatccca aaaagccggt    780
ctcagttcgg attgcaggct gcaactcgcc tgcatgaagc cggaattgct agtaatcgcg    840
gatcagcatg ccgcggtgaa tacgttcccg ggtcttgtac acaccgcccg t              891
```

<210> SEQ ID NO 23
<211> LENGTH: 891
<212> TYPE: DNA
<213> ORGANISM: Bacillus sp.

<400> SEQUENCE: 23

```
acgggcggtg tgtacaagac ccgggaacgt attcaccgca gcatgctgat ctgcgattac     60
tagcgattcc ggcttcatgc aggcgagttg cagcctgcaa tccgaactga gaatggtttt    120
ttgggattag ctccacctcg cggtatcgca gccctttgta ccatccattg tagcacgtgt    180
gtagcccagg tcataagggg catgatgatt tgacgtcatc cccaccttcc tccgactttt    240
agccggcagt ctccttagag tgcccaactg aatgctggca actaaggaca agggttgcgc    300
tcgttgcggg acttaaccca acatctcacg acacgagctg acgacaacca tgcaccacct    360
gtcatcctgt ccccgaaggg aaagccctat ctctagggtg gtcaggagat gtcaagacct    420
ggtaaggttc ttcgcgttgc ttcgaattaa accacatgct ccaccgcttg tgcgggtccc    480
cgtcaattcc tttgagtttc agtcttgcga ccgtactccc caggcggagt gcttaatgcg    540
ttagctgcag cactgaaggg cggaaaccct ccaacactta gcactcatcg tttacggcgt    600
ggactaccag ggtatctaat cctgtttgct ccccacgctt tcgcgcctca gcgtcggatc    660
cggcccagcc ggccgccttc gccacgggtg ttcttcccga tctctacgca ttccaccgct    720
acaccgggaa ttccaccggc ccctaccggt ccctagacag gcagtatcaa gagcagctcc    780
ggggttgagc cccagaattt caccccctgac ttgcaccgtc cgcctgcgcg cgctttacgc    840
ccagtaattc cgaacaacgc tcgcgccctc cgtcttaccg cggctgctgg c              891
```

<210> SEQ ID NO 24
<211> LENGTH: 889
<212> TYPE: DNA
<213> ORGANISM: Desulfotomaculum geothermicum
<400> SEQUENCE: 24

```
gccagcagcc gcggtaacac gtaggggggcg agcgttgtcc ggaatcactg ggcgtaaagg     60
gagcgtaggc ggccttgtgt gtcctgcgtg aaaggcgccg gcttaaccgg cgaaggtcgt    120
gggaaactgc agggcttgag tgccggagag ggtggcggaa ttcccggtgt agcggtgaaa    180
tgcgtagata tcgggaggaa caccagtggc gaaggcggcc acctggacgg taactgacgc    240
tgaggctcga aagctggggg agcaaacagg attagatacc ctggtagtcc cagccgtaaa    300
cgatgggtgc taggtgttgt gggctttgag cctgctgtgc cgtaggacac ccaataagca    360
```

```
cccccgcctgg ggagtacggc cgcaaggttg aaactcaaag gaattgacgg gggcccgcac      420
aagcggtgga gcatgtggtt taattcgaag caacgcgaag aaccttacca ggccttgaca      480
tcgcccggaa agccatggaa acatggcccct cctttttggac cgggtgacag gtggtgcatg    540
gtcgtcgtca gctcgtgtcg tgagatgttg ggttaagtcc cgcaacgagc gcaacccttg      600
agcttagttg ccagcacctg gggtgggcac tctaggctga ctgccggtga caaaccggag      660
gaaggcgggg atgacgtcaa atcatcatgc cccttatgac ctgggctaca cacgtgctac      720
aatggccggt acaaagggcc gcgaaggagc gatccggagc caatcccaaa aagccggtct      780
cagttcggat tgcaggctgc aactcgcctg catgaagccg gaattgctag taatcgcgga      840
tcagcatgcc gcggtgaata cgttcccggg ccttgtacac accgcccgt                  889

<210> SEQ ID NO 25
<211> LENGTH: 893
<212> TYPE: DNA
<213> ORGANISM: Xanthomonas sp.

<400> SEQUENCE: 25
gccagcagcc gcggtaatac gtaggggggcg agcgttgtcc ggaatcactg ggcgtaaagg       60
gcgtgtaggc ggttcgttaa gtccggggtg aaagcccacg gctcaaccgt gggactgcct      120
tggaaactgg cggacttgag ggcaggagag ggaagcggaa ttcccggtgt agcggtgaaa      180
tgcgtagata tcgggaggaa caccagtggc gaaggcggct tcctggcctg tccctgacgc      240
tgaggcgcga cagcgtgggg agcgaacggg attagatacc ctggtagtcc acgccctaaa      300
cgatgcgaac tggatgttgg gttcaatcgg gaactcagta tcgaagctaa cgcgttaagt      360
tcgccgcctg gggagtacgg tcgcaagact gaaactcaaa ggaattgacg ggggcccgca      420
caagcggtgg agtatgtggt ttaattcgat gcaacgcgaa gaaccttacc tggccttgac      480
atccagggaa ccctgcagag atgcgggggt gccttcggga accctgagac aggtgctgca      540
tggctgtcgt cagctcgtgt cgtgagatgt tgggttaagt cccgcaacga gcgcaaccct      600
tgtccttagt tgccagcacg taatggtggg aactctaagg agactgccgg tgacaaaccg      660
gaggaaggtg gggatgacgt caagtcatca tggcccttac ggccagggct acacacgtac      720
tacaatggga aggacagagg gctgcgaacc cgcgaggggg agccaatccc agaaaccttc      780
tctcagtccg gattggagtc tgcaactcga ctccatgaag tcggaatcgc tagtaatcgc      840
agatcagcat tgctgcggtg aatacgttcc cgggccttgt acacaccgcc cgt             893

<210> SEQ ID NO 26
<211> LENGTH: 893
<212> TYPE: DNA
<213> ORGANISM: Bacillus horti

<400> SEQUENCE: 26
acgggcggtg tgtacaaggc ccgggaacgt attcaccgcg gtatgctgac ccgcgattac       60
tagcgattcc gccttcacgc aggcgagttg cagcctgcga tccgaactga gaccggcttt      120
ctcggattcg ctccaggtcg cccccttcgct tccgtctgta ccggccattg tagcacgtgt     180
gtagcccagg ccataagggg catgatgatc tgacctcatc cccaccttcc tccggtttgt      240
caccggcagt ccccctagag tgcccaccca cggtgttggc aactaaggggc gagggttgcg     300 ctcgttgcgg gacttaaccc aacatctcac gacacgagct gacgacaacc atgcaccacc      360 tgtctccccct gtcccgaaag ggcctgcccc atctctggaa cattcagggg gatgtcaaga    420
cctggtaagg ttcttcgcgt tgcttcgaat taaaccacat gctccactgc ttgtgcgggt      480
```

```
cccgtcaat tcctttgagt ttcaaccttg cggccgtact ccccaggcgg agtgcttagt      540
gcgttagctc cggcacggga ggggtcgata cctcccacac ctagcactca tcgtttacgg     600
cgtggactac cagggtatct aatcctgttt actccccacg ctttcgcgcc tcagcgtcag     660
ttacaggcca gagagctgcc ttcgccatcg gtgttcctcc tgatctctac gcatttcacc     720
gctacaccag gaattccact ctcctctcct gcactcaagt cccccagttt ccaatggccc     780
tccacggttg agccgtgggc tttcacatca gacttaaggg accgcctgcg cgcgctttac     840
gcccaatgat tccggacaac gcttgccccc tacgtattac cgcggctgct ggc           893
```

<210> SEQ ID NO 27
<211> LENGTH: 886
<212> TYPE: DNA
<213> ORGANISM: unknown
<220> FEATURE:
<223> OTHER INFORMATION: Backwater bioreactor bacterium with closest
       match to GenBank AF394170

<400> SEQUENCE: 27

```
acgggcggtg tgtacaagac ccgggaacgt attcaccgcg acatgctgat ccgcgattac      60
tagcgattcc gacttcatgc agtcgagttg cagactgcaa tccggactac gatcgggttt     120
ctggattagc tccccctcg cgggttggca gccctctgtc ccgaccattg tatgacgtgt      180
gaagccctac ccataagggc catgaggacc tgacgtcatc cccaccttcc tccggtttgt     240
caccggcagt ctcattagag tgcccttttcg tagcaactaa tgacaagggt tgcgctcgtt     300
gcgggactta acccaacatc tcacgacacg agctgacgac ggccatgcag cacctgtgtt     360
ccggttctct ttcgagcact cccaaatctc ttcgggattc cggacatgtc aagggtaggt     420 aaggttttc gcgttgcatc gaattaatcc acatcatcca ccgcttgtgc gggtccccgt      480
caattccttt gagttttaat cttgcgaccg tactccccag gcggagtgct taatgtgtta     540
acttcggcac cgaaaggtta gtcccctccg acacctagca ctcatcgttt acggcgtgga     600
ctaccagggt atctaatcct gtttgctccc cacgctttcg cgcctcagcg tcagttacag     660
cccagaaagc cgccttcgcc actggtgttc ctccatatct ctacgcattt caccgctaca     720 catgaattc cgcttccctc tgctgcactc aagtcctcca gtttccagtg cgcagcaggg     780
ttgagccccg ctcttataca ccagacttaa aggaccgcct gcgcgcgctt tacgcccaat    840
aattccggac aacgctcgcc ccctacgtat taccgcggct gctggc                    886
```

<210> SEQ ID NO 28
<211> LENGTH: 890
<212> TYPE: DNA
<213> ORGANISM: Brevibacillus borstelensis

<400> SEQUENCE: 28

```
gccagcagcc gcggtaatac gtaggtggca agcgttgtcc ggaattattg ggcgtaaagc      60
gcgcgcaggc ggctatgtaa gtctggtgtt aaagcccggg gctcaacccc ggttcgcatc     120
ggaaactgtg tagcttgagt gcagaagagg aaagcggtat ccacgtgta gcggtgaaat     180 gcgtagagat gtggaggaac accagtggcg aaggcggctt tctggtctgt aactgacgct     240
gaggcgcgaa agcgtgggga gcaaacagga ttagatacc tggtagtcca cgccgtaaac     300
gatgagtgct aggtgttggg ggtttcaata ccctcagtgc cgcagctaac gcaataagca     360
ctccgcctgg ggagtacgct cgcaagagtg aaactcaaag gaattgacgg gggcccgcac     420
aagcggtgga gcatgtggtt taattcgacg caacgcgaag aaccttacca gcccttgaca     480
```

```
tgcccggacg gtttccagag atggattcct cccagcaatg ggcccgggaca caggtgctgc    540 atggctgtcg tcagctcgtg tcgtgagatg ttgggttaag tcccgcaacg agcgcaaccc    600
tcgccactag ttgccatcat taagttgggc actctagtgg gactgccggt gataagccgg    660
aggaaggtgg ggatgacgtc aagtcatcat ggcccttatg ggctgggcta cacacgtgct    720
acaatggcgg tgacaatggg cagccaccca gcgatgggga gctaatccca aaaagccgtc    780
tcagttcgga tcgcaggctg caactcgcct gcgtgaaggc ggaatcgcta gtaatcgccg    840
gtcagcaaac ggcggtgaat acgttcccgg gccttgtaca caccgcccgt              890
```

<210> SEQ ID NO 29
<211> LENGTH: 686
<212> TYPE: DNA
<213> ORGANISM: Carboxydobrachium pacificus
<400> SEQUENCE: 29

```
acgggcggtg tgtacaaggc ccgggaacgt attcaccgcg gcatggctga tccgcgatta     60
ctagcgattc cggcttcatg cagtcgagtt gcagactgca atccgaactt agaccggctt    120
tctgggattc gctccccctc acgggttcgc agccctctgt accggccatt gtagcacgtg    180
tgtcgccctg ggcgtaaggg ccatgatgac ttgacatcat ccccaccttc ctccggcttg    240
gcgccggcag tcccccgaga gtcctcggct ttacccgtta gcaacacggg cagggggttg    300
cgctcgttgc gggacttaac ccaacaccctc acggcacgag ctgacgacaa ccatgcacca    360
cctgtgccgg ctcccggccc gaagaccggg tcggtcgcct ttcggctccc tacctccggc    420
atgtcaagcc ctggtaaggt tcttcggtta gcatcgaatt aaaccacatg ctccaccgca    480
tgtgcgggcc cccgtcaatt cctttgagtt tcaaccttgc ggccgtactc cccaggcggg    540
gtgcttaatg cgttagctgc ggcacggagg gcctacaccc ccacaccta gcacccatcg    600 tttacggcgt ggactaccgg ggtatctaat cccgttcgct ccccacgctg tcgcgcctca    660
gcgtcaggga caggccagga agccgc                                          686
```

<210> SEQ ID NO 30
<211> LENGTH: 891
<212> TYPE: DNA
<213> ORGANISM: Geobacter hephaestius
<400> SEQUENCE: 30

```
acgggcggtg tgtacaaggc ccgggaacgt attcaccgcg gtatgctgac ccgcgattac     60
tagcgattcc gccttcacgc aggcgagttg cagcctgcga tccgaactga gaccggcttt    120
ctcggattgc tccaggtcg ccccttcgct tccgtctgta ccggccattg tagcacgtgt    180
gagcccaggc cataaggggc atgatgatct gacctcatcc ccaccttcct ccggtttgtc    240
accggcagtc ccttagagt gcccacccac ggtgttggca actaagggcg agggttgcgc    300
tcgttgcggg acttaaccca acatctcacg acacgagctg acgacagcca tgcagcacct    360
gtgcacgtgt cccgaaggag ggcccctgtt tccagaggct ttcacgtgca tgtcaagccc    420
aggtaaggtt cttcgcgttg cttcgaatta aaccacatgc tccaccgctt gtgcgggccc    480
ccgtcaattc ctttgagttt cagccttgcg gccgtactcc caggcgggg tgcttaacgc    540 gttagctacg acaccgaaag ggtcgctccc cccggcatct agcacccatc gtttacggcg    600
tggactacca gggtatctaa tcctgtttgc tccccacgct ttcgcgcctc agcgtcagtt    660
acaggccaga gagctgcctt cgccatcggt gtttctcctg atctctacgc atttcaccgc    720
```

```
tacaccagga attccactct cctctcctgc actcaagtcc cccagttttcc aatggccctc     780 cacggttgag ccgtgggctt tcacatcaga cttaagggac cgcctgcgcg cgctttacgc     840
ccaatgattc cggacaacgc ttgcccccta cgtattaccg cggctgctgg c              891
```

<210> SEQ ID NO 31
<211> LENGTH: 892
<212> TYPE: DNA
<213> ORGANISM: Bacillus schlegelii

<400> SEQUENCE: 31

```
gccagcagcc gcggtaagac ggagggcgcg agcgttgttc ggaattactg ggcgtaaagc      60
gcgcgcaggc ggacggtgca agtcagggg gaaattctgg ggctcaaccc cggagctgct     120
cttgatactg cctgtctagg accggtagg ggccggtgga attcccggtg tagcggtgaa     180
atgcgtagat atcgggagga acaccagtgg cgaaggcggc ttcctggcct gtccctgacg    240
ctgaggcgcg acagcgtggg gagcgaacgg gattagatac cccggtagtc cacgccgtaa    300
acgatgggtg ctaggtgtgg gtgggttcga ccccatccgt gccgtagcca acgcaataag    360
caccccgcct ggggagtacg gccgcaaggc tgaaactcaa aggaattgac ggggccccgc    420
acaagcggtg gagcatgtgg tttaattcga agcaacgcga agaaccttac ccgggcttga    480
catctcccgg aagtcgtcag agatggcggc gtcccgcaag ggactgggag acaggtggtg    540
catggttgtc gtcagctcgt gtcgtgagat gttgggttaa gtcccgcaac gagcgcaacc    600
cttgagctta gttgccagca cctggggtgg cactctagg ctgactgccg gtgacaaacc    660
ggaggaaggc ggggatgacg tcaaatcatc atgccccctta tgacctgggc tacacacgtg    720
ctacaatggc ggtgacaatg ggcagccact cagcgatgag gagctaatcc ctaaaagccg    780
tctcagttcg gattgagctc tgcaactcga gctcatgaag tcggaatcgc tagtaatcgc    840
ggatcagcat gccgcggtga atacgttccc gggccttgta cacaccgccc gt            892
```

<210> SEQ ID NO 32
<211> LENGTH: 890
<212> TYPE: DNA
<213> ORGANISM: Pedomicrobium ferrugineum

<400> SEQUENCE: 32

```
acgggcggtg tgtacaaggc ccgggaacgt attcaccgcc gtttgctgac cggcgattac      60
tagcgattcc gccttcacgc aggcgagttg cagcctgcga tccgaactga ggccggcttt    120
aagggattgg cttcccctca cggggtcgca acccgctgta ccggccattg tagcatgtgt    180
gtagcccagg gcatccaggg catgatgatt tgacgtcatc cccgccttcc tccggcttat    240
caccggcagt cccactagag tgcccaactt aatgatggca actagtggcg agggttgcgc    300
tcgttgcggg acttaaccca acatctcacg acacgagctg acgacagcca tgcagcacct    360
gtgtcccggc ccattgctgg gaggaatcca tctctggaaa ccgtccggc atgtcaaggg    420 ctggtaaggt tcttcgcgtt gcgtcgaatt aaaccacatg ctccaccgct tgtgcgggcc    480
cccgtcaatt cctttgagtt ttaaccttgc ggccgcactc cccaggcggg atgcttaacg    540
cgttagctgc gccaccgaca agcaagcttg ccgacggcta gcatccatcg tttacggcgt    600
ggactaccag ggtatctaat cctgttcgct ccccacgctt tcgctcctca gcgtcagtag    660
cggcccagag accgccttc gccaccggtg ttcctcctga tatctgcgca tttcaccgct    720
acaccaggaa ttccagtctc ctctcctgca ctcaagtccc ccagtttcca atggccctcc    780
acggttaagc cgtgggcttt cacatcagac ttaagggacc gcctgcgcgc gctttacgcc    840
```

-continued

```
caatgattcc ggacaacgct tgcccCctac gtattaccgc ggctgctggc           890

<210> SEQ ID NO 33
<211> LENGTH: 890
<212> TYPE: DNA
<213> ORGANISM: Photorhabdus luminescens

<400> SEQUENCE: 33
acgggcggtg tgtacaaggc ccgggaacgt attcaccgtg gcattctgat ccacgattac    60
tagcgattcc gacttcatgg agtcgagttg cagactccaa tccggactac gacgcacttt   120
atgaggtccg cttgctctcg cgaggtcgct tctctttgta tgcgccattg tagcacgtgt   180
gtagccctgg tcgtaagggc catgatgact tgacgtcatc cccaccttcc tccagtttat   240
cactggcagt ctcctttgag ttcccggccg gaccgctggc aacaaaggat aagggttgcg   300
ctcgttgcgg gacttaaccc aacatttcac aacacgagct gacgcagcc atgcagcacc    360 tgtctcacgg ttcccgaagg cacattctca tctctgaaaa cttccgtgga tgtcaagacc   420
aggtaaggtt cttcgcgttg catcgaatta accacatgc tccaccgctt gtgcgggccc    480
ccgtcaattc atttgagttt taaccttgcg gccgtactcc ccaggcggtc gacttaacgc   540
gttagctccg gaagccacgc ctcaagggca caacctccaa gtcgacatcg tttacggcgt   600
ggactaccag ggtatctaat cctgtttgct ccccacgctt tcgcacctga gcgtcagtct   660
tcgtccaggg ggccgccttc gccaccggta ttcctccaga tctctacgca tttcaccgct   720
acacctggaa ttctaccccc ctctacgaga ctcaagcttg ccagtatcag atgcagttcc   780
caggttgagc ccggggattt cacatctgac ttaacaaacc gcctgcgtgc gctttacgcc   840
cagtaattcc gattaacgct tgcaccctcc gtattaccgc ggctgctggc              890

<210> SEQ ID NO 34
<211> LENGTH: 898
<212> TYPE: DNA
<213> ORGANISM: Thermoanaerobacter keratinophilus

<400> SEQUENCE: 34
gccagcagcc gcggtaagac ggagggcgca agcgttactc ggaattactg ggcgtaaagc    60
gtgcgtaggt ggttcgctaa gtctgatgtg aaagccctgg gctcaacctg gaactgcat    120 tggatactgg cgggctagag tgcggtagag ggcagtggaa ttcctggtgt agcagtgaaa   180
tgcgtagaga tcgggaggaa caccagtggc gaaggcggct acctggacgg tccctgacgc   240
tgaggcacga aagctggggg agcaaacagg attagatacc ctggtagtcc cagccgtaaa   300
cgatgggtgc taggtgtggg gggtgtaggc cctccgtgcc gcagctaacg cattaagcac   360
cccgcctggg gagtacggcc gcaaggttga aactcaaagg aattgacggg gcccgcaca    420 agcggtggag catgtggttt aattcgatgc taaccgaaga accttaccag gcttgacat    480 gccggaggta gggagccgaa aggcgaccga cccggtcttc gggccgggag ccggcacagg   540
tggtgcatgt tgtcgtctg ctcgtgccgt gaggtgttgg gttaagtccc gcaacgagcg   600
caacccctgc cccgtgttgc taacgggcga gccgagcact cgcgggggac tgccggcgac   660
aagccggagg aaggcgggga tgacgtcaaa tcatcatgcc ctggatgccc tgggctacac   720
acatgctaca atggtcggta cagcgggttg cgacccgtg aggggagcc aatccctcaa    780 agccggcctc agttcggatc gcaggctgca actcgcctgc gtgaaggcgg aatcgctagt   840
aatcgccggt cagcaaacgg cggtgaatac gttcccgggc cttgtacaca ccgcccgt    898
```

<210> SEQ ID NO 35
<211> LENGTH: 892
<212> TYPE: DNA
<213> ORGANISM: unknown
<220> FEATURE:
<223> OTHER INFORMATION: Uncultured bacterium with closest match to
      GenBank AY563464

<400> SEQUENCE: 35

```
gccagcagcc gcggtaatac gtaggggcg agcgttgtcc ggaatcactg ggcgtaaagg      60
gagcgtaggc ggccttgtgt gtcctgcgtg aaaggcgccg gcttaaccgg cgaaggtcgt     120
gggaaactgc agggcttgag tgccggagag ggtggcggaa ttcccggtgt agcggtgaaa    180
tgcgtagata tcgggaggaa caccagtggc gaaggcggcc acctgacgg taactgacgc     240
tgaggctcga aagctggggg agcaaacagg attagatacc ctggtagtcc cagccgtaaa    300
cgatgggtgc taggtgttgt gggctttgag cctgctgtgc cgtaggacac ccaataagca    360
ccccgcctgg ggagtacggc cgcaaggctg aaactcaaag gaattgacgg gggcccgcac    420
aagcggtgga gtatgtggtt taattcgatg caacgcgaag aaccttacct ggccttgaca    480
tccagggaac cctgcagaga tgcggggtg ccttcgggaa ccctgagaca ggtgctgcat     540
ggctgtcgtc agctcgtgtc gtgagatgtt gggttaagtc ccgcaacgag cgcaacccct    600
gtccttagtt gccagcacgt aatggtggga actctaagga gactgccggt gacaaaccgg    660
aggaaggtgg ggatgacgtc aagtcatcat ggcccttacg gccagggcta cacacgtact    720
acaatgggaa ggacagaggg ctgcgaaccc gcgaggggga gccaatccca gaaaccttct    780
ctcagtccgg attggagtct gcaactcgac tccatgaagt cggaatcgct agtaatcgca    840
gatcagcatt gctgcggtga atacgttccc gggccttgta cacaccgccc gt            892
```

<210> SEQ ID NO 36
<211> LENGTH: 891
<212> TYPE: DNA
<213> ORGANISM: Georgenia sp.

<400> SEQUENCE: 36

```
acgggcggtg tgtacaagac ccgggaacgt attcaccgcg gcatggctga tccgcgatta     60
ctagcgattc cggcttcatg cagtcgagtt gcagactgca atccgaactt agaccggctt    120
tctgggattc gctcccccctc acgggttcgc agccctctgt accggccatt gtagcacgtg   180
tgtcgccctg ggcgtaaggg ccatgatgac ttgacatcat ccccaccttc ctccggcttg    240
gcgccggcag tcccccgaga gtcctcggct ttacccgtta gcaacacggg gcaggggttg    300
cgctcgttgc gggacttaac ccaacatctc acgacacgag ctgacgacaa ccatgcacca    360
cctgtatacc ggccttgcgg ggcacccatc tctgggtgtt ccggtatat gtcaagccct     420
ggtaaggttc ttcgcgttgc atcgaattaa tccgcatgct ccgccgcttg tcgggcccc     480
cgtcaattcc tttgagtttt agccttgcgg ccgtactccc caggcggggc gcttaatgcg    540
ttagctgcgg cacggaactc gtggaatgag ccccacacct agcgcccaac gtttacggcg    600
tggactacca gggtatctaa tcctgttcgc tccccacgct ttcgctcctc agcgtcagta    660
gcggcccaga gacccgcctt cgccaccggt gttcctcctg atatctgcgc atttcaccgc    720
tacaccagga attccagtct cccctaccgc actctagtct gcccgtatcc accgcaagcc    780
gagagttaag ccccggttt tcacggcaga gcgacaaac cgcctacgag ctctttacgc     840
ccaataattc cggacaacgc tcgcacccta cgtattaccg cggctgctgg c              891
```

<210> SEQ ID NO 37
<211> LENGTH: 893
<212> TYPE: DNA
<213> ORGANISM: unknown
<220> FEATURE:
<223> OTHER INFORMATION: Uncultured wastewater bacterium with closest
      match to GenBank AF309817

<400> SEQUENCE: 37

```
gccagcagcc gcggtaatac gaagggtgca agcgttactc ggaattactg ggcgtaaagc      60
gtgcgtaggt ggttcgctaa gtctgatgtg aaagccctgg gctcaacctg gaactgcat     120
tggatactgg cgggctagag tgcggtagag ggcagtggaa ttcctggtgt agcagtgaaa    180
tgcgtagaga tcaggaggaa cacccgtggc gaaggcgact gcctggacca gtactgacac    240
tgaggcacga aagcgtgggg agcaaacagg attagatacc ctggtagtcc acgccctaaa    300
cgatgcgaac tggatgctgg gttcaatcgg gaactcagta tcgaagctaa cacattaagc    360
actccgcctg gggagtacgg ccgcaaggct gaaactcaaa ggaattgacg ggacccgca     420
caagcagtgg agcatgtggt ttaattcgaa gcaacgcgaa gaaccttacc aggtcttgac    480
atccccctga atgttccaga gatggggcag gcccttcgg gacaggggag acgggtggtg     540
catggttgtc gtcagctcgt gtcgtgagat gttgggttaa gtcccgcaac gagcgcaacc    600
cttgagctta gttgccagca cttggggtgg gcactctagg ctgactgccg gtgacaaacc    660
ggaggaaggc ggggatgacg tcaaatcatc atgccccta tgacctgggc tacacacgtg     720
ctacaatggc cggtacaaag ggccgcgaag gagcgatccg gagccaatcc caaaaagccg    780
gtctcagttc ggattgcagg ctgcaactcg cctgcatgaa gccggaattg ctagtaatcg    840
cggatcagca tgccgcggtg aatacgttcc cgggtcttgt acacaccgcc cgt           893
```

<210> SEQ ID NO 38
<211> LENGTH: 705
<212> TYPE: DNA
<213> ORGANISM: unknown
<220> FEATURE:
<223> OTHER INFORMATION: Uncultured bacterium with closest match to
      GenBank AY309172
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (75)..(75)
<223> OTHER INFORMATION: n is a, c, g, or t
<220> FEATURE:
<221> NAME/KEY: misc_feature
<222> LOCATION: (100)..(100)
<223> OTHER INFORMATION: n is a, c, g, or t
<220> FEATURE:
<221> NAME/KEY: misc_feature
<222> LOCATION: (110)..(111)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t
<220> FEATURE:
<221> NAME/KEY: misc_feature

```
<222> LOCATION: (121)..(122)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (166)..(167)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (232)..(232)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (331)..(333)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (449)..(449)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t
<220> FEATURE:
<221> NAME/KEY: misc_feature
<222> LOCATION: (472)..(473)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
```

```
<221> NAME/KEY: misc_feature
<222> LOCATION: (491)..(497)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (529)..(530)
<223> OTHER INFORMATION: n is a, c, g, or t
<220> FEATURE:
<221> NAME/KEY: misc_feature
<222> LOCATION: (539)..(540)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t
<220> FEATURE:
<221> NAME/KEY: misc_feature
<222> LOCATION: (583)..(584)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (589)..(589)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (604)..(604)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (623)..(623)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t
<220> FEATURE:
<221> NAME/KEY: misc_feature
<222> LOCATION: (703)..(703)
<223> OTHER INFORMATION: n is a, c, g, or t

<400> SEQUENCE: 38
gccagcagcc gcggtaacac gnagggggcn ngcgttgcnc ggaatcactg ggcgtaaagg     60
```

```
gtgcgtaggc ggatntacta agtcctgggt gaaatccccn ggctcaaccn nggaanngct      120
nntgatactg gnggtcttga gtcccggaga ggttagtgga attccnngtg tagnggtgaa      180
atncgtagat atcaggagga acaccagtgg cgaaggcggc tccctggacc gnccctgacg      240
ctgaggngcg aaagctgggg gagcaaacag gattagatac cctggtagtc ccngccgtaa      300
acgatggatg ctagncgtng gggntgtngg nnntccgtgn cgcagctaac gcnttaagca      360
ncccgcctgg ggagtacggc cgcaaggttg aaactcaaag gaattgacgg gggcccgcac      420
aagcggtgga gcatgtggtt taattcgang ctanccgaag aaccttacca gnncttgaca      480
tgcccgaant nnnnnnnncaa atggattccn acccggnctt cggcgccgnn agacgtgcnn      540
acgtggctgc atgnctgctc gtcgnctcgn gncgttgagg tgnngnncnt aagtccngcg      600
aacnanctcg aacacctgtt gcnatgttgc taantgggca ctctagtcac tcctgccggt      660
aatgccggcg aanaacgtga ggatgacgtc atgacgtcta tcntt                      705

<210> SEQ ID NO 39
<211> LENGTH: 891
<212> TYPE: DNA
<213> ORGANISM: unknown
<220> FEATURE:
<223> OTHER INFORMATION: Uncultured bacterium with closest match to
      GenBank AB021333

<400> SEQUENCE: 39
gccagcagcc gcggtaatac gcagggtgca agcgttactc ggaattactg ggcgtaaaac       60
gtgcgtaggt ggttcgctaa gtctgatgtg aaagccctgg gctcaacctg gaactgcat      120 tggatactgg cgggctggag tgcggtagag ggcagtggaa ttcctggtgt agcagtgaaa      180
tgcgtagaga tcaggaggaa cacccgtggc gaaggcgact gcctggacca gtactgacac      240
tgaggcacga aagcgtgggg agcaaacagg attagatacc ctggtagtcc acgccctaaa      300
cgatgcgaac tggatgttgg gttcaatcgg gaactcagta tcgaagctaa cgcgttaagt      360
tcgccgcctg gggagtacgg tcgcaagact gaaactcaaa ggaattgacg ggggcccgca      420
caagctgtgg agtatgtggt ttaattcgat gcaacgcgaa gaaccttacc tggccttgac      480
atccagggaa ccctgcagag atgcgggggt gccttcggga accctgagac aggtgctgca      540
tggctgtcgt cagctcgtgt cgtgagatgt tgggttaagt cccgcaacga gcgcaaccct      600
tgagcttagt tgccagcacc tggggtgggc actctaggct gactgccggt gacaaaccgg      660
aggaaggcgg ggatgacgtc aaatcatcat gccccttatg acctgggcta cacacgtgct      720
acaatggccg gtacaaaggg ccgcgaagga gcgatccgga gccaatccca aaaagccggt      780
ctcagttcgg attgcaggct gcaacttgcc tgcatgaagc cggaattgct agtaatcgcg      840
gatcagcatg ccgcggtgaa tacgttcccg ggtcttgtac acaccgcccg t              891
```

METHOD TO ENHANCE BIODEGRADATION OF SULFONATED ALIPHATIC-AROMATIC CO-POLYESTERS BY ADDITION OF A MICROBIAL CONSORTIUM

FIELD OF THE INVENTION

The invention relates to a microbial consortium having the ability to biodegrade sulfonated aliphatic-aromatic co-polyesters having more than 60 mol percent aromatic acid content based on total acid content and a method of degrading such polyesters.

BACKGROUND OF THE INVENTION

Synthetic polymers, including poly-ethylene, -styrene, and -propylene, must retain their functionality over widely varying conditions of temperature and pressure fluctuation, flame exposure, etc. They are consequently synthesized to have backbones of only carbon atoms, which makes them resistant to chemical and enzymatic degradation. Introducing heteroatoms into the polymer backbone creates functional groups, such as esters and amines. These groups increase the polyester's susceptibility to hydrolytic cleavage, i.e. degradation, thereby improving the polyester's ability to biodegrade upon disposal. Moreover, polyester polymers are susceptible to hydrolytic cleavage when exposed to chemical or enzymatic treatment Many polyester polymers, especially when made of aliphatic monomers, e.g. polyhydroxybutyrate and poly($\epsilon$-caprolactone), are considered biodegradable (Muller et al., *J Biotechnol*, 86:87-95 (2001); Abou-Zeid et al., *J Biotechnol*, 86:113-126 (2001)). But, aliphatic polyesters lack commercially valuable material properties, like durability, because of their low melting temperatures and increased susceptibility to degradation. In contrast, aromatic polyesters, exemplified by polyethylene terephthalate (PET), have desired durability but are in the main considered non-biodegradable or have unacceptably slow biodegradation rates. (See Kint, D. and Munoz-Guerra, S., (1999) *Polym Int* 48:346-352).

The balance between functionality and biodegradability is an important consideration in achieving cost-effective waste disposal. Disposable single-use items of aliphatic polyesters are environmentally attractive but generally lack acceptable durability, whereas such items of aromatic polyesters have the preferred functionality but are ecologically burdensome.

A partial resolution to this dilemma is the use of aliphatic-aromatic co-polyesters, which have durability and other preferred attributes and are biodegradable as well. However, the use of high aromatic content co-polyesters in disposable single-use items is still not entirely satisfactory because the rate of biodegradation is proportional to the content of aromatic acid in the co-polyester. The problem in optimizing functionality and biodegradability is that increasing aromatic content improves utility but decreases biodegradability (U.S. Pat. No. 6,521,717 to Itoh, H. and German Patent Application DE 19508737 to Witt et al.).

One strategy for increasing susceptibility to hydrolytic cleavage of these co-polyesters is to treat them with hydrolytic enzymes before or after the co-polyesters enter the waste cycle. Numerous enzymes, known in the art, can degrade polymers containing hydrolyzable groups, such as esters, amides, etc.

For example, U.S. Pat. No. 6,255,451 to Koch et al. describes the use of a cutinase from *Humicola insolens* and lipases from *Aspergillus niger, Mucor Miehei* (Lipozyme 20,000 L), and *Candida antartica* (lipase component B) to degrade substrate polymers that are aliphatic polyesters, aromatic polyester amides or partially aromatic polyester urethanes. International App. No. PCT/US04/16349 to Nagarajan, corresponding to U.S. patent application Ser. No. 10/852,403, which are incorporated herein by reference, describe a method to increase the biodegradation rate of aliphatic-aromatic co-polyesters having more than 60 mol percent aromatic acid content by contacting the co-polymer with at least one hydrolytic enzyme. U.S. Pat. No. 6,066,494 to Hsich et al. and U.S. Pat. No. 6,254,645 to Kellis et al. describe the use of lipases or polyesterases to modify polyester fiber to enhance wettability and absorbancy of textiles. U.S. Pat. No. 6,350,607 to Cooney, Jr. discusses the use of enzymes for treatment of macerated food waste products in conjunction with garbage disposal apparatus. U.S. Pat. No. 5,464,766 to Bruno reports waste treatment compositions containing bacteria and enzymes for municipal and yard waste. However, using purified or partially purified enzymes is often expensive. Plus, processes based on enzymatic pretreatment of the co-polymer followed by composting may not be the most efficient process to degrade aliphatic-aromatic co-polyesters having greater than 60 mol percent aromatic acid content because the mixture of endogenous microbes in the composting system may not be optimally adapted to completely mineralize the polymeric waste.

One way to increase the biodegradation rate of high aromatic content co-polyesters is to use a microbial consortium that has been adapted to biodegrade aliphatic-aromatic co-polyesters, especially sulfonated ones, having greater than 60 mol percent aromatic acid content. To biodegrade such co-polyesters, the microbial consortium must be able to cleave the polymer backbone and mineralize the subsequent products formed.

The problem to be solved is the development of an economical method to increase the rate of biodegradation in typical composting conditions of sulfonated aliphatic-aromatic co-polyesters having more than 60 mol percent aromatic acid content relative to the total acid content. This problem has been solved in the invention described herein, which provides a new microbial consortium (SPDC-1) capable of accelerating the biodegradation of sulfonated aliphatic-aromatic co-polyesters having more than 60 mol percent aromatic acid content relative to the total acid content of the polymer. This invention is economical, fosters the use of composting as a workable waste process, can help eliminate the need for source separation of waste, can provide commercially valuable fertilizer-quality compost and can help accelerate the rate of degradation of high aromatic polyesters disposed in landfills.

SUMMARY OF THE INVENTION

The invention described herein provides a consortium of microbes (SPDC-1; ATCC PTA-6129) useful for biodegrading sulfonated aliphatic-aromatic co-polyesters, the co-polyester comprising at least one sulfonated compound, said sulfonated compound comprising between about 0.1 to about 10.0 mol percent of the co-polyester, based on total diol or total dicarboxylic acid in the co-polyester, at least one aromatic dicarboxylic acid or an ester thereof, and at least one aliphatic dicarboxylic acid or an ester thereof, the aromatic acid comprising greater than 60 mol percent to about 99 mol percent of total dicarboxylic acid in the co-polyester.

Also provided is a method of using microbial consortium SPDC-1 (ATCC PTA-6129) to biodegrade sulfonated aliphatic-aromatic co-polyesters having greater than 60 mol percent aromatic acid content based on total diol or total dicarboxylic acid in the co-polyester, comprising:

providing a microbial consortium SPDC-1 having ATCC accession number PTA-6129;

contacting the microbial consortium of a) under suitable reaction conditions with a sulfonated aliphatic-aromatic co-polyester having more than 60 mol percent aromatic acid content based on total diol or total dicarboxylic acid in the co-polyester; and growing said microbial consortium under said suitable conditions whereby the co-polyester is degraded.

BRIEF DESCRIPTION OF THE SEQUENCES

Figure 1:
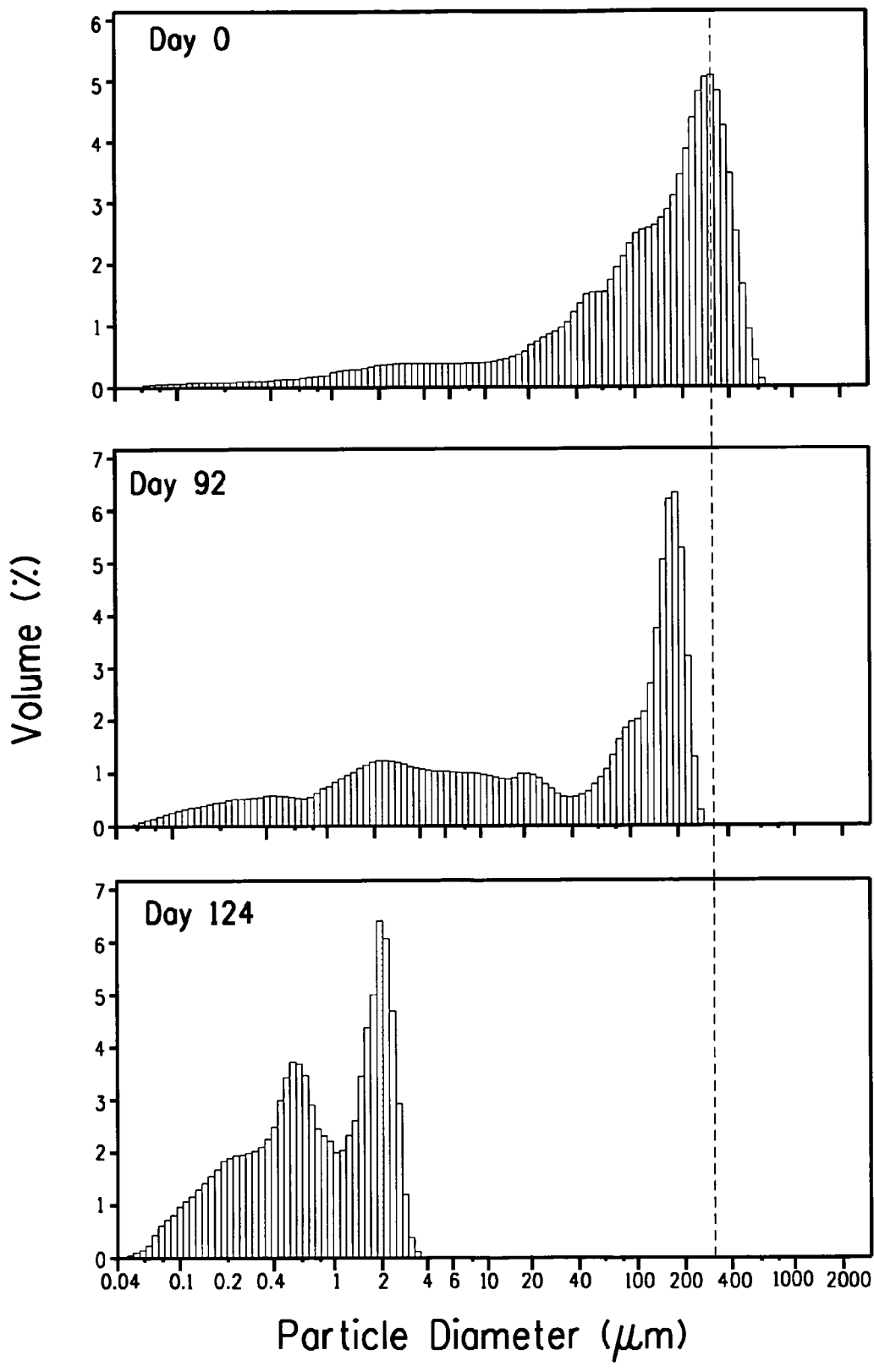
FIG. 1 shows size distribution of aliphatic-aromatic polyester particles in a bioreactor.

The following sequences comply with 37 C.F.R. 1.821-1.825 ("Requirements for patent applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO: 1 is the nucleotide sequence of primer JCR14.

SEQ ID NO: 2 is the nucleotide sequence of primer JCR15.

SEQ ID NO: 3 is the nucleotide sequence of universal primer M13 forward.

SEQ ID NO: 4 is the nucleotide sequence of universal primer M13 reverse.

SEQ ID NO: 5 is the nucleotide sequence of the 16S rRNA gene isolated from bacterial strain SPDC1-1.

SEQ ID NO: 6 is the nucleotide sequence of the 16S rRNA gene isolated from bacterial strain SPDC1-2.

SEQ ID NO: 7 is the nucleotide sequence of the 16S rRNA gene isolated from bacterial strain SPDC1-3.

SEQ ID NO: 8 is the nucleotide sequence of the 16S rRNA gene isolated from bacterial strain SPDC1-20.

SEQ ID NO: 9 is the nucleotide sequence of the 16S rRNA gene isolated from bacterial strain SPDC1-4.

SEQ ID NO: 10 is the nucleotide sequence of the 16S rRNA gene isolated from bacterial strain SPDC1-5.

SEQ ID NO: 11 is the nucleotide sequence of the 16S rRNA gene isolated from bacterial strain SPDC1-6.

SEQ ID NO: 12 is the nucleotide sequence of the 16S rRNA gene isolated from bacterial strain SPDC1-8.

SEQ ID NO: 13 is the nucleotide sequence of the 16S rRNA gene isolated from bacterial strain SPDC1-10.

SEQ ID NO: 14 is the nucleotide sequence of the 16S rRNA gene isolated from bacterial strain SPDC1-11.

SEQ ID NO: 15 is the nucleotide sequence of the 16S rRNA gene isolated from bacterial strain SPDC1-12.

SEQ ID NO: 16 is the nucleotide sequence of the 16S rRNA gene isolated from bacterial strain SPDC1-13.

SEQ ID NO: 17 is the nucleotide sequence of the 16S rRNA gene isolated from bacterial strain SPDC1-18.

SEQ ID NO: 18 is the nucleotide sequence of the 16S rRNA gene isolated from bacterial strain SPDC1-14.

SEQ ID NO: 19 is the nucleotide sequence of the 16S rRNA gene isolated from bacterial strain SPDC1-15.

SEQ ID NO: 20 is the nucleotide sequence of the 16S rRNA gene isolated from bacterial strain SPDC1-16.

SEQ ID NO: 21 is the nucleotide sequence of the 16S rRNA gene isolated from bacterial strain SPDC1-17.

SEQ ID NO: 22 is the nucleotide sequence of the 16S rRNA gene isolated from bacterial strain SPDC1-19.

SEQ ID NO: 23 is the nucleotide sequence of the 16S rRNA gene isolated from bacterial strain SPDC1-23.

SEQ ID NO: 24 is the nucleotide sequence of the 16S rRNA gene isolated from bacterial strain SPDC1-31.

SEQ ID NO: 25 is the nucleotide sequence of the 16S rRNA gene isolated from bacterial strain SPDC1-35.

SEQ ID NO: 26 is the nucleotide sequence of the 16S rRNA gene isolated from bacterial strain SPDC1-22.

SEQ ID NO: 27 is the nucleotide sequence of the 16S rRNA gene isolated from bacterial strain SPDC1-24.

SEQ ID NO: 28 is the nucleotide sequence of the 16S rRNA gene isolated from bacterial strain SPDC1-25.

SEQ ID NO: 29 is the nucleotide sequence of the 16S rRNA gene isolated from bacterial strain SPDC1-26.

SEQ ID NO: 30 is the nucleotide sequence of the 16S rRNA gene isolated from bacterial strain SPDC1-29.

SEQ ID NO: 31 is the nucleotide sequence of the 16S rRNA gene isolated from bacterial strain SPDC1-30.

SEQ ID NO: 32 is the nucleotide sequence of the 16S rRNA gene isolated from bacterial strain SPDC1-32.

SEQ ID NO: 33 is the nucleotide sequence of the 16S rRNA gene isolated from bacterial strain SPDC1-33.

SEQ ID NO: 34 is the nucleotide sequence of the 16S rRNA gene isolated from bacterial strain SPDC1-34.

SEQ ID NO: 35 is the nucleotide sequence of the 16S rRNA gene isolated from bacterial strain SPDC1-37.

SEQ ID NO: 36 is the nucleotide sequence of the 16S rRNA gene isolated from bacterial strain SPDC1-38.

SEQ ID NO: 37 is the nucleotide sequence of the 16S rRNA gene isolated from bacterial strain SPDC1-41.

SEQ ID NO: 38 is the nucleotide sequence of the 16S rRNA gene isolated from bacterial strain SPDC1-42.

SEQ ID NO: 39 is the nucleotide sequence of the 16S rRNA gene isolated from bacterial strain SPDC1-43.

Biological Deposit

The following biological deposit was made under the terms of the Budapest Treaty on the International Recognition of the Deposit of Microorganisms for the Purposes of Patent Procedure:

| Depositor Identification Reference | International Depository Designation | Date of Deposit |
|---|---|---|
| Microbial consortium SPDC-1 | ATCC PTA-6129 | Jul. 23, 2004 |

As used herein, "ATCC" refers to the American Type Culture Collection International Depository Authority located at ATCC, 10801 University Blvd., Manassas, Va. 20110-2209, U.S.A. The "International Depository Designation" is the accession number to the culture on deposit with ATCC.

The listed deposit will be maintained in the indicated international depository for at least thirty (30) years and will be made available to the public upon the grant of a patent disclosing it. The availability of a deposit does not constitute a license to practice the subject invention in derogation of patent rights granted by government action.

DETAILED DESCRIPTION OF THE INVENTION

The present microbial consortium ("SPDC-1") can degrade sulfonated aliphatic-aromatic co-polyesters having greater than 60-mol percent aromatic acid content relative to the total acid content of the polymer. SPDC-1 was deposited on Jul. 23, 2004 to the American Type Culture Collection (accession number PTA-6129).

SPDC-1 was prepared by selecting microorganisms from mature compost for their ability to work together to biodegrade sulfonated aliphatic-aromatic co-polyesters having more than 60 mol percent aromatic acid content. The consortium was selected for its ability to both hydrolyze the backbone of the co-polyester into smaller polymeric fragments and/or monomers and utilize the released low molecular weight fragments and/or monomers as a carbon source for growth. This consortium can be added as a seed to any compost— or an aqueous bioreactor mimicking composting conditions—that contains the sulfonated aliphatic-aromatic co-polyester having more than 60 mol percent aromatic acid content relative to the total acid content of the co-polyester. The present consortium can be used alone or in combination with other microorganisms to biodegrade and/or accelerate biodegradation of the present sulfonated aliphatic-aromatic co-polyesters.

Also described herein are methods to biodegrade and/or accelerate the biodegradation of sulfonated aliphatic-aromatic copolyester waste. Specifically, these methods increase the rate of biodegradation of sulfonated high aromatic co-polyesters by treatment with microbial consortium SPDC-1. Such treatment accelerates the overall biodegradation of sulfonated high aromatic co-polyesters by increasing the degradation of the polymer backbone and providing a mixture of microbes capable of using the various degradation products (i.e. monomers, etc.) for growth (i.e. suitable carbon source).

Definitions

As used herein, "microbial consortium SPDC-1" and "SPDC-1" refer to the microbial consortium sample deposited to the American Type Culture Collection (ATCC) on Jul. 23, 2004 having accession number PTA-6129. SPDC-1 comprises a variety of bacteria, many of which are identifiable by their unique 16S rRNA gene sequences provided herein (Table 2; SEQ ID NOs: 5-39). One of skill in the art can use the present 16S rRNA gene sequences to identify many of the bacterial strains in microbial consortium SPDC-1.

As used herein, "high aromatic co-polyester" refers to aliphatic-aromatic polyesters containing more than 60 mol percent aromatic diacids relative to the total acid content of the polyester, such as terephthalic acid.

As used herein, "aliphatic-aromatic co-polyester" refers to a co-polyester for which some of the aliphatic diacid building blocks have been substituted by aromatic diacids.

As used herein, "greater than 60 mol percent diacid content" refers to "greater than 60 mol percent dicarboxylic acid content" and to "greater than 60 mol percent diacid content" and are all equivalent. In this discussion, the aliphatic-aromatic polyesters comprise aliphatic dicarboxylic acids and aromatic dicarboxylic acids wherein the aromatic acid content (as measured relative to the total dicarboxylic acid content) is greater than 60 mol percent.

As used herein, "total acid content" and "based on total dio or dicarboxylic acid" are equivalent and refer to the total content of aromatic plus aliphatic dicarboxylic acid in the aliphatic-aromatic co-polyester.

As used herein, "sulfonated aliphatic-aromatic co-polyester", "sulfonated co-polyester", "sulfonated co-polyester of interest", and "sulfonated high aromatic co-polyester of interest" refer a co-polyester containing at least one 5-sulfoisophthalic acid derivative as one of the constituent monomers and contains greater than 60 mol percent aromatic dicarboxylic acid, typically terephthalic acid; less than 40 mol percent aliphatic dicarboxylic acid, such as glutaric, adipic, and succinic acids; 0.1-10 mol percent—optionally 0.1 mol percent to 5.0 mole percent—of said 5-sulfoisophthalic acid derivative such as 5-sulfoisophthalic acid and which may specifically be 0.1-3 mol percent dimethyl-5-sulfoisophthalic acid sodium salt; and optionally a diol such as ethylene glycol, 1,3-propanediol, and 1,4-butanediol. These are also referred to as "co-polyesters of interest".

As used herein, "hydrolytic enzymes" refer to a class of hydrolases that include, but are not limited to proteases, lipases, cutinases and esterases.

As used herein, "hydrolysis" refers to the primary mechanism of action in degrading polymers primarily invoked by hydrolytic enzymes. It includes the breaking of ester and amide linkages from the polymer backbone by the addition of water mediated by hydrolytic enzymes to result in the parent carboxylic acid group and the respective functional group, that is, the hydroxyl functional group for esters (i.e. alcohols such as methanol) and the appropriate amine for amides. This is also known as hydrolytic degradation of the polymer backbone.

As used herein, "lipase" refers to an enzyme that catalyzes the hydrolysis of fats into glycerol and fatty acids by hydrolyzing ester bonds.

As used herein, "cutinase" refers to a hydrolytic enzyme that degrades cutin, the cuticular polymer of higher plants, which is a polyester composed of hydroxy and epoxy fatty acids. The fatty acids of cutin are usually n-$C_{16}$ and n-$C_{18}$ and contain one to three hydroxyl groups. Ester bonds predominate in the cutins, although peroxide bridges and ether linkages may also be present.

As used herein, "esterase" and "polyesterase" are used interchangeably to refer to an enzyme that catalyzes the hydrolysis of an ester.

As used herein, "protease" refers to an enzyme that catalyzes the hydrolytic breakdown of proteins via hydrolysis of peptide bonds. "Biodegradable" or "degradable" describes polymers that can be broken down chemically by natural biological processes, such as being digested by bacteria or fungi into smaller components not harmful to the environment.

As used herein, "biodegradation by microbial action" or "biodegradation" refers to what is believed to be a two step process of the break down of co-polyesters. In the first step, hydrolytic enzymes secreted by microorganisms break down the polymer backbone of the co-polyesters into monomers and/or smaller fragments; in the second step, microorganisms, either the same or different as in the first step, take up the monomers and broken down fragments and catabolize them into biomass, biogas, and liquid leachate.

As used herein, "rate of biodegradation/biodegradability" refers to the time required or rate at which biodegradation occurs. This varies depending on temperature, humidity, exposure to air, etc. in the waste context of the disposed co-polyester of interest. The absolute rate of biodegradation for a specific waste context is difficult to compute with precision, as biodegradation is a unique characteristic of specific waste conditions and specific waste mass.

As used herein, "enhance biodegradation", "increase biodegradation" or "accelerate biodegradation" are equivalent and refer to a characteristic of the action of the microbial consortion described herein. Polyesters of interest are generally regarded by those of skill in the art as not biodegradable or to have such slow rate of biodegradation as to be effectively not biodegradable. The action of the consortium described herein has the characteristic of either initiating biodegradation or speeding up the rate of biodegradation already begun naturally.

As used herein, "waste context" refers to and includes composting, landfill, solid waste, wastewater treatment system, septic tank system, and garbage disposal systems.

As used herein, "composting" refers to a process of degrading waste materials under conditions no higher than about 70° C., and averaging more nearly about 55-60° C., at or near 100 percent relative humidity, and for durations ranging from two weeks to more than several months. The materials continue to degrade into low molecular weight fragments and/or monomers which can ultimately be biodegraded, that is, metabolized by microorganisms, completely into biomass, biogas, and liquid leachate. "Composting system" or "composting apparatus" refers to a vessel, apparatus, or enclosure where composting occurs. Typically, the composting system will include microorganisms and material to composted. The composting system may also be a bioreactor.

As used herein, "bioreactor" refers to a container (or several containers connected in series or parallel) for growing and/or maintaining living organisms for production or biodegradation of one or more target materials. The bioreactor container can be of any size and it is contemplated to include fermentors (using batch and/or continuous fermentation methodology), waste treatment systems, and wastewater treatment systems.

As used herein, "waste treatment system" refers to a context where and a process in which a co-polyester of interest is contacted under suitable aerobic conditions with SPDC-1 for biodegradation into biomass, biogas, and liquid leachate. The process may also be performed using at least one microorganism isolated from SPDC-1. A waste treatment system may include continuous or batch fermentation systems, commercial waste treatment systems, and composting systems.

As used herein, commercial waste treatment systems are well known in the art and may be "a wastewater treatment system", which involves a multi-stage process to remove the organics in the wastewater before it reenters a body of water, or is applied to the land or reused. Generally, the first stage comprises screening out solid debris (i.e. the sulfonated co-polyester). In a subsequent stage, separated sulfonated co-polyester is biodegraded in the presence of a microbial consortium for a period of time in a bioreactor (See Metcalf and Eddy, *Wastewater Engineering Treatment and Reuse*, 4$^{th}$ Ed., Tchobanoglous, G., Burton, F., and Stensel, H., Editors, McGraw-Hill Inc., New York, N.Y. (2003)).

As used herein, "compost tea" refers to a liquid (aqueous) extract from compost that contains soluble nutrients and a diverse mix of microorganisms capable of growing on the decaying compost material.

As used herein, "landfill" refers to a solid waste context, generally in an anaerobic environment at the temperature of the ambient air or adjacent soil in relatively low humidity. A landfill pit is lined with plastic and/or clay into which solid waste is dumped, isolated from ground water and air, and kept dry, thereby preventing microbial action from breaking down the waste, which, as a result, degrades slowly.

As used herein, "contacting" is equivalent to "treating" and refers to placing SPDC-1 in contact with a sulfonated co-polyester such that biodegradation process can occur. "Treatment" refers to contacting microbial consortium SPDC-1 with a co-polyester at any point during the cycle of use and disposal of the sulfonated co-polyester and includes the concepts of "pre-treatment" of the sulfonated co-polyester before disposal and "post-treatment" after disposal. "Contacting" includes spraying, treating, pouring on or in, mixing, combining, painting, coating, applying, affixing to and otherwise communicating microbial consortium SPDC-1 with the sulfonated co-polyester.

As used herein, "other biodegradable compounds" refers to substances besides sulfonated aliphatic-aromatic co-polyesters that are able to decay naturally, harmlessly and relatively more quickly than high aromatic co-polyesters. These include starch, protein, cellulose, beeswax, montan-ester wax, leather, paper, fabric, fillers, such as calcium carbonate, calcium carbonate phosphates, and titanium dioxide, cellulosic fillers, silicate fillers, such as silicon dioxide, biodegradable adhesives, polylactic acid, polyhydroxyamide and mixtures of these.

As used herein, "biodegradable" or "degradable" refers to compounds that can be broken down by natural biological processes, such as mineralization by bacteria or fungi, into smaller components that may eventually be use to generate biomass and byproducts of microbial metabolism.

As used herein, "suitable reaction conditions" refers to temperature, acidity/alkalinity and/or humidity at which the biodegradation performed by the microbial consortia of the present invention occurs and further includes either a growth or reaction supplementation to the microbial consortia of the present invention.

As used herein, "isolated nucleic acid fragment" refers to a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

As used herein, "plasmid", "vector", and "cassette" refer to an extrachromosomal element often carrying genes, which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

As used herein, "percent identity", as known in the art, refers to a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Infor-*

*matics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs (BLASTP, BLASTN, BLASTX (Altschul et al., *J. Mol. Biol.* 215:403-410 (1990)). Sequence alignments and percent identity calculations may be performed using the Megalign program of the LASER-GENE bioinformatics computing suite (DNASTAR Inc., Madison, Wis.) or the AlignX program of Vector NTI v. 7.0 (Informax, Inc., Bethesda, Md.). Multiple alignments of the sequences can be performed using the Clustal method of alignment (Higgins and Sharp, *CABIOS,* 5: 151-153 (1989)) with the default parameters (GAP PENALTY=10, GAP LENGTH PENALTY=10). Default parameters for pairwise alignments using the Clustal method are typically KTUPLE 1, GAP PENALTY=3, WINDOW=5 and DIAGONALS SAVED=5.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to, the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNAS-TAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.), Vector NTI (Informax, Bethesda, Md.) and Sequencher v. 4.05. Within the context of this application it will be understood that where sequence analysis software is used for analysis, that the results of the analysis will be based on the "default values" of the program referenced, unless otherwise specified.

As used herein, "default values" refer to any set of values or parameters set by the software manufacturer that originally load with the software when first initialized.

Abbreviations

The following abbreviations are used throughout:
polyethylene terephthalate PET
polybutylene terephthalate PBT
polyethylene ether radical consisting of —(CH2)2-O—(CH2)2-DEG
polyethylene ether radical consisting of —(CH2)2-O—(CH2)2-O—(CH2)2-TEG
of ethylene —(CH2)-, —(CH2)3-3G
—(CH2)4-4G
carbon dioxide $CO_2$
Polylactic acid PLA
Polyhydroxyamide PHA
Weight wt
Mole mol
Polymerase chain reaction PCR Sulfonated Aliphatic-Aromatic Co-Polymers Biodegraded by these Methods The methods described herein increase the rate of biodegradation of sulfonated aliphatic-aromatic co-polymers through treatment of the polymers with a microbial consortium optimized to biodegrade such compositions. Sulfonated co-polyesters, which contain in chain ester groups that are derived from the condensation of a diacid with a diol or from the polymerization of hydroxyacids, are degradable because they possess functional groups, such as esters, amides and urethanes, which are susceptible to hydrolysis, i.e., hydrolytic cleavage. Cleaving the polymer backbone through hydrolysis of these functional groups mediated by a hydrolytic enzyme creates smaller polymer fragments of monomers that microorganisms can take up and then metabolize into biomass, biogas (i.e. $CO_2$), and liquid leachate.

In aliphatic polyesters, the diacid component is predominantly an aliphatic acid; these polymers are exemplified by polyhydroxy alkanoates produced by microorganisms or synthetic polymers such as poly caprolactone or poly lactide. Aromatic polyesters are polymers such as polyethylene terephthalate (PET) or polybutylene terephthalate (PBT) in which the diacid component is an aromatic acid such as terephthalic acid or ester thereof. Many of the preferred material characteristics of polyesters, such as thermal stability, gas and liquid permeability, etc., are related to the relative amount of aromatic monomers in the polyester. Aromatic polyesters make up, for example, throwaway plastic beverage bottles. These are generally considered difficult-to impossible-to-biodegrade because the aromatic acid used, such as terephthalic acid, makes the polymer backbone resistant to hydrolytic degradation.

Aliphatic-aromatic co-polyesters are polyesters derived from a mixture of aromatic diacids, e.g. terephthalic acid or ester derivatives thereof, and aliphatic diacids which are typically linear polyalkylene groups, $C_2$ to $C_{10}$ in length. Muller et al. (supra) report that non-sulfonated aliphatic-aromatic co-polyesters containing more than 60 mol percent terephthalic acid as diacid relative to the total acid content are considered essentially non-biodegradable (or at least very slow to degrade) and therefore non-compostable.

The aliphatic dicarboxylic acid component may include unsubstituted, substituted, linear, and branched, aliphatic dicarboxylic acids and the lower alkyl esters of aliphatic dicarboxylic acids having 2 to 36 carbon atoms. Specific examples of an aliphatic dicarboxylic acid component include oxalic acid, dimethyl oxalate, malonic acid, dimethyl malonate, succinic acid, dimethyl succinate, methylsuccinic acid, glutaric acid, dimethyl glutarate, 2-methylglutaric acid, 3-methylglutaric acid, adipic acid, dimethyl adipate, 3-methyladipic acid, 2,2,5,5-tetramethylhexanedioic acid, pimelic acid, suberic acid, azelaic acid, dimethyl azelate, sebacic acid, 1,11-undecanedicarboxylic acid, 1,10-decanedicarboxylic acid, undecanedioic acid, 1,12-dodecanedicarboxylic acid, hexadecanedioic acid, docosanedioic acid, tetracosanedioic acid, dimer acid, and mixtures of these. Particularly useful are the following: succinic acid, dimethyl succinate, glutaric acid, dimethyl glutarate, adipic acid, dimethyl adipate and mixtures of these. However, these lists are not intended as inclusive and any aliphatic dicarboxylic acid component known in the art may be useful in the present method.

The aromatic dicarboxylic acid component includes unsubstituted and substituted aromatic dicarboxylic acid and the lower alkyl esters of aromatic dicarboxylic acids having from 8 carbons to 20 carbons. Examples of desirable diacid moieties include those derived from terephthalates, isophthalates, naphthalates and dibenzoates. Specific examples of the aromatic dicarboxylic acid component include terephthalic acid, dimethyl terephthalate, isophthalic acid, dimethyl isophthalate, 2,6-napthalene dicarboxylic acid, dimethyl-2,6- naphthalate, 2,7-naphthalenedicarboxylic acid, dimethyl-2,7-naphthalate, 3,4'-diphenyl ether dicarboxylic acid, dimethyl-3,4'diphenyl ether dicarboxylate, 4,4'-diphenyl ether dicarboxylic acid, dimethyl-4,4'-diphenyl ether dicarboxylate, 3,4'-diphenyl sulfide dicarboxylic acid, dimethyl-3,4'-diphenyl sulfide dicarboxylate, 4,4'-diphenyl sulfide dicarboxylic acid, dimethyl-4,4'-diphenyl sulfide dicarboxylate, 3,4'-diphenyl sulfone dicarboxylic acid, dimethyl-3,4'-diphenyl sulfone dicarboxylate, 4,4'-diphenyl sulfone dicarboxylic acid, dimethyl-4,4'-diphenyl sulfone dicarboxylate, 3,4'-benzophenonedicarboxylic acid, dimethyl-3,4'-benzophenonedicarboxylate, 4,4'-benzophenonedicarboxylic acid, dimethyl-4,4'-benzophenonedicarboxylate, 1,4-naphthalene dicarboxylic acid, dimethyl-1,4-naphthalate, 4,4'-methylene bis(benzoic acid), dimethyl-4,4'-methylenebis(benzoate), and mixtures of these. Particularly useful are the following aromatic dicarboxylic acid components: terephthalic acid, dimethyl terephthalate, isophthalic acid, dimethyl isophthalate, 2,6-naphthalene dicarboxylic acid, dimethyl-2,6-naphthalate, and mixtures of these. Any aromatic dicarboxylic acid component known in the art may be useful in these methods.

The aromatic acid may comprise any of the following percentages of total acid content of the co-polyester: over 60 mol percent up to 99 mol percent; about 61 mol percent up to about 90 mol; at least 70 mol percent up to about 90 mol percent; at least 80 mol percent up to about 90 mol percent; at least 90 mol percent up to about 99 mol percent of the total acid content; at least 95 mol percent up to about 99 mol percent of the total diacid content of the co-polyester; or at least 97 mol percent up to about 99 mol percent of the total acid content of the co-polyester.

Sulfonated co-polyesters have been reported. See U.S. Pat. Nos. 5,171,308, 5,171,309, 5,219,646 to Gallagher, et. al.; U.S. Pat. No. 5,295,985 to Romesser et al.; U.S. Pat. Nos. 6,018,004 and 6,297,347 to Warzelhan et al., and U.S. Pat. No. 6,368,710 to Hayes (the last incorporated herein by reference). The sulfonated co-polyesters of interest should include an aliphatic dicarboxylic acid component of between about 1 and less than about 40 mol percent of the total diacid content, or between about 10 and less than 40 mol percent based on total diacid content, or between about 20 and less than 40 mol percent. An example of an aliphatic sulfonate component includes the metal salts of sulfosuccinic acid.

These co-polyesters of interest should also include, based on total diacid content, an aromatic dicarboxylic acid component of between greater than 60 and 99 mole percent or greater than 60 mol percent up to about 90 mole percent or between 70 and 90 mol percent or between 80 and 90 mol percent based on total diacid content. Examples of useful aromatic sulfonate components as endgroups include the metal salts of 3-sulfobenzoic acid, 4-sulfobenzoic acid, and 5-sulfosalicylic acid.

Useful sulfonate components are those in which the sulfonate salt group is attached to an aromatic dicarboxylic acid, the aromatic nucleus of which may be benzene, naphthalene, diphenyl, oxydiphenyl, sulfonyldiphenyl, methylenediphenyl or the like. A useful sulfonate monomer includes the residue of a sulfonate-substituted phthalic acid, terephthalic acid, isophthalic acid, 2,6-naphthalenedicarboxylic acid. A particularly useful sulfonate component is the metal salt of 5-sulfoisophthalic acid or the lower alkyl esters of 5-sulfoisophthalate. The metal salt may be monovalent or polyvalent alkali metal ions, alkaline earth metal ions, or other metal ions and the like. The alkali metal ion may be sodium, potassium or lithium and alkaline earth metals, such as magnesium, are also useful. Other useful metal ions include the transition metal ions, such as zinc, cobalt or iron. In one embodiment, the sulfo group-containing component is between about 0.1 mol percent to about 10 mol percent of the sulfonated co-polyester compositions. These methods are particularly useful when the sulfo group-containing component is in the 0.1 to 5.0 mol percent incorporation level within the sulfonated co-polyester of interest.

Useful diol components in the co-polyesters of interest include glycols containing from 2 to 12 carbon atoms, glycol ethers containing from 4 to 12 carbon atoms and polyether glycols having the structural formula $HO(AO)_nH$, wherein A is an alkylene group containing from 2 to 6 carbon atoms and n is an integer from 2 to 400. Generally, such polyether glycols will have a molecular weight from about 400 to 4000. The glycols will normally contain from 2 to 8 carbon atoms, but typically from 4 to 8 carbon atoms. Some representative examples of glycols that can be used as the diol component include 1,2-ethane diol, 1,3-propane diol, 1,4-butane diol, 1,6-hexane diol, ethylene glycol, di(ethylene glycol), tri(ethylene glycol), poly(ethylene)glycol, 1,3-propylene glycol, 1,2-propylene glycol, 2,2-diethyl-1,3-propanediol, 2,2-dimethyl-1,3-propane diol, 2-ethyl-2-butyl-1,3-propane diol, 2-ethyl2-isobutyl-1,3-propane diol, 1,3-butane diol, 1,5-pentane diol, 2,2,4-trimethyl-1,6-hexane diol, 1,3-cyclohexane dimethanol, 1,4-cyclohexane dimethanol, 2,2,4,4,-tetramethyl-1,3-cyclobutane diol, isosorbide, poly(alkylene ether) glycols, poly(propylene ether)glycols and the like.

Other biodegradable compounds may be combined with the co-polyesters of interest. These compounds include starch, protein, cellulose, beeswax, montan-ester wax, leather, paper, fabric, fillers, such as calcium carbonate, calcium carbonate phosphates, and titanium dioxide, cellulosic fillers, silicate fillers, such as silicon dioxide, biodegradable adhesives, polylactic acid, polyhydroxyamide and mixtures of these.

A particularly useful sulfonated co-polyester of interest is known as "Polymer B", which comprises poly(ethylene terephthalate) with 17.5 mol percent DBE-5 (dimethyl glutarate, CAS # 1119-40-0, based on 100 mol percent total acids), 2 mol percent DRL-6 (dimethyl 5-sulfoisophthalate, sodium salt, CAS # 3965-55-7), and 8 wt. percent poly(ethylene glycol), (1000 MW, bop). The sulfonated co-polyesters of interest may exist as a particle, film or be laminated.

The Process of Biodegradation

Biodegradation in composting occurs by what is believed to be a two-step process. In the first step, hydrolytic enzymes are applied to the solid waste typically by microorganisms present in the compost, which secrete the hydrolytic enzymes. The rate and overall amount of hydrolytic enzyme secretion observed under composting conditions may be very low for complete biodegradation of aliphatic-aromatic co-polyesters. The first step is believed to involve secretion of hydrolytic enzymes from microbes within the composting environment. These hydrolytic enzymes cleave the polyester backbone into lower molecular weight compounds and monomers via hydrolysis, which is a process in which a molecule is cleaved in two by the addition of a molecule of water. This process can occur both chemically and enzymatically. In a hydrolysis reaction that involves breaking an ester bond, one hydrolysis product contains a hydroxyl functional group, and the other a carboxylic acid functional group. Amides hydrolyze to the parent carboxylic acid and the corresponding amine.

It has been shown that exogenously supplied hydrolytic enzymes greatly increase the rate of biodegradation of aromatic-aliphatic co-polyesters (See Nagarajan, V.; PCT/US04/16349 corresponding to U.S. Ser. No. 10/852,403).

The second step of biodegradation is that microorganisms capable of metabolizing the low molecular weight compounds/monomers catabolize these into biomass, biogas, and liquid leachate. The catabolizing microorganisms may be the same or different from those that secreted the enzymes. The bulk of the low molecular weight compounds/monomers resulting from degradation of the polymer backbone include terephthalic acid, aliphatic acid(s), hydroxyacids(s), and glycols.

A variety of microorganisms have been reported to be able to metabolize the monomers used to make aliphatic-aromatic copolyesters. For example, microorganisms have been reported which catabolize terephthalic acid. See Bramucci et al., *Appl Microbiol Biotechnol*, 58:255-259 (2002); U.S. Pat. Nos. 6,187,569 and 6,461,840 to Bramucci et al.; and Junker, F. and Cook, A., *Appl Environ Microbiol*, 63:2403-2410 (1997).

The methods described herein use a microbial consortium SPDC-1 (ATCC No. PTA-6129) to accelerate or enhance the biodegradation of sulfonated aliphatic-aromatic co-polyesters having more than 60 mol percent aromatic acid content. It is also contemplated that one or more of the microorganisms identified within SPDC-1 may be isolated and used to biodegrade the sulfonated co-polyesters of interest. The 16S rRNA gene sequences for the most prevalent species found within microbial consortium SPDC-1 are listed in Table 2. One of skill in the art can isolate and/or identify one or more strains listed in Table 2 using the growth conditions and the 16S rRNA gene sequences described herein.

SPDC-1 was developed using selective pressure to obtain a unique mixture of microbes having the ability to work together to optimally biodegrade the present sulfonated aliphatic-aromatic co-polyesters having greater than 60 mol percent aromatic acid content based on the total dicarboxylic acid in the co-polyester. The selection was performed in a bioreactor using environmental conditions that can be observed under typical composting conditions. As such, the microbial consortium selected from the bioreactor experiments should be useful in any composting system.

In contrast to composting is landfilling, the deposition of solid waste into a carefully-designed structure built into or on top of the ground in which solid waste is isolated from groundwater, air and rain. The temperature is that of the surrounding soil or ambient air, humidity is low and the conditions are typically anaerobic, which prevents degradation by microbial action and results in a relatively slow breakdown over the course of decades and even longer, instead of months or years in compost. Somewhat differently, a bioreactor landfill operates to more rapidly transform and degrade solid waste by the addition of liquid and air, which enhances microbial processes of degradation similar to those in composting.

Accelerating Biodegradation: the Present Method

The methods described herein increase, i.e., accelerate or enhance, the rate of biodegradation of sulfonated aliphatic-aromatic co-polyesters having greater than 60 mol percent aromatic acid content and is useful in most waste contexts, including composting, landfilling and wastewater treatment systems. Because such co-polyesters are generally considered not biodegradable or to have such a slow rate of biodegradation as to be effectively not biodegradable, the technical solution of these methods is to provide a microbial consortium selected for its ability to biodegrade these co-polyesters. Consequently, contacting the microbial consortium or isolated bacteria strains described herein to these co-polyesters can both initiate the process of their biodegradation as well as accelerate the rate of any minimal level biodegradation already begun naturally.

Microbial Consortium Treatment: Contacting Microbial Consortium SPDC-1 (ATCC PTA-6129) to the Co-Polyester In order to increase the rate of biodegradation of sulfonated aliphatic-aromatic co-polyesters having greater than 60 mol percent aromatic acid content based on total acid content, the methods described herein provide a treatment step in which microbial consortium SPDC-1 is contacted to the co-polyesters of interest either before or after disposal. In a typical composting environment, a complex mixture of microbes acts together to degrade a variety of organic materials. The waste can be a complex mixture of solid waste or waste primarily comprised of sulfonated aliphatic-aromatic co-polyesters. Thus, treatment of the compostable waste with the present microbial consortium provides a mixture of microbes selected for their ability to specifically biodegrade sulfonated co-polymers, thereby decreasing their overall biodegradation time.

The process of contacting includes any kind of treatment of the co-polyester by SPDC-1, including but not limited to: spraying, painting, coating, pouring, mixing, applying, etc. The terms "pre-treatment", "post-treatment" and "treatment" are interchangeable and refer to contacting SPDC-1 to the co-polyesters of interest.

The mechanics of contacting the co-polyesters of interest with SPDC-1 depend on the nature of the disposed items as well as on the expected disposal route. In one contacting context, after waste collection, which may include the collection of recyclables, solid non-recyclable waste may be separated out. To the non-recyclable waste may be applied an aqueous solution that comprises between about 0.1 to about 10.0 weight percent of SPDC-1 so that the aqueous solution contacts the co-polyesters of interest. Such contacting may comprise spraying the solid waste.

Another contacting context may involve coating with an aqueous solution of SPDC-1 the items comprising the co-polyesters of interest, before or after being disposed. Alternatively, such items may be painted with or dipped in aqueous solution of SPDC-1. The methods described here contemplate virtually any manner of contacting the co-polyester of interest with an aqueous solution of SPDC-1. Moreover, contacting solid waste with multiple applications of SPDC-1 is contemplated.

There are at least two stages in the waste treatment process when the present method would be useful. In the initial screening for solid debris prior to its deposition in a land fill, a solution comprised of SPDC-1 may be contacted with the solid debris at any point after screening up to the deposition of the debris into a landfill; and later, when sludge and scum have entered the digester, a solution comprised of SPDC-1 may be added to the digester to accelerate degradation. And, of course, the grit and/or digested material may be contacted with SPDC-1 after its deposition in a landfill.

Simulation of Compost with Aquatic Bioreactor

Compost is a complex heterogeneous environment that contains diverse microorganisms, complex material and inorganic particulate matter. It is difficult to achieve and maintain consistent operating conditions from one experiment to another and standard analytical methods do not apply easily. An aquatic bioreactor was designed to evaluate the effects of hydrolyic enzyme treatment on sulfonated aliphatic-aromatic co-polyesters. The use of aqueous reaction systems to characterize the biodegradability or compostability of polymers has been reported previously, facilitating control of experimental variables. See Kleeberg et al., supra; Gouda et al., supra; and German testing standard DIN V54900, Deutsches Institut für Normberg 1998 *Testing of the compostability of polymeric materials*, parts 1-3.

For these methods, the conditions within the aquatic bioreactor were very similar to those found in a composting environment (55° C.-60° C., 100 percent relative humidity). Data obtained from the aquatic bioreactor experiments herein parallel those obtained from a composting system (municipal or otherwise). Ultimately, the determination that waste biodegradation has accelerated relies on the measurement of the remaining amount of solid polymer in the bioreactor after enzymatic treatment.

Bioreactor

The Bioreactors, that is "Bioreactor BF2" and "Bioreactor BF4", used in the present examples were 1-L dished bottom reactors. The bioreactors were stirred to provide continuous agitation and fitted to a controller to maintain the pH at about 6.5 to about 8.5 (targeted to about pH 8.0). A circulating water bath was used to pass water through the bioreactor jacket so as to maintain a constant temperature inside of the bioreactor. Air was bubbled through the bioreactor culture medium at a flow rate of 50 mL/min.

Compost Tea

Compost tea was prepared as reported in the literature with slight modification. Approximately 50 g of mature yard compost was added to 400 mL of SMV1 medium, divided equally into two 1-L Erlenmeyer flasks. The flasks were incubated in a shaking water bath at 55° C. for 16 h. The top portion of the liquid (supernatant) in each flask was combined (about 350 mL total; the "compost tea") and mixed with about 650 mL SMV1 in bioreactor BF2 on day 0.

Measurement of Degradation

Numerous methods for measuring polymer degradation are known in the art, which include physical observation, gravimetric analysis, biogas (i.e. carbon dioxide) production, biomass accumulation, characterization of degradation products (for example, using standard analytical techniques such as GC, LC, MS, UV, etc.), and particle size analysis. Specifically, the amount of solid polymer measured before and after treatment can be used to determine the speed of degradation per unit time. Additionally, samples can be taken to measure the relative size and concentration of polymer particulate over time in response to various conditions using an optical particle size analyzer. The ability of one or more microorganisms to use the polymer as a carbon source can be measured by an increase in overall biomass.

Culturing Systems

A classical batch culturing method is a closed system in which the composition of the medium is set at the beginning of the culture and not subject to artificial alterations during the culturing process. At the beginning of the culturing process, the medium is inoculated with the desired organism(s) and metabolic activity is permitted to occur adding nothing to the system. A "batch" culture is batch with respect to the addition of carbon source; attempts are often made to control pH and oxygen concentration. In batch systems the metabolite and biomass compositions of the system change constantly up to the time the culture is terminated. Within batch cultures cells experience a static lag phase, then high growth log phase and finally a stationary phase with halted growth. If untreated, cells in the stationary phase will eventually die. Cells in log phase are often responsible for the bulk of production of end product or intermediate in some systems. Stationary or post-exponential phase production can be obtained in other systems.

A variation is the Fed-Batch system, which is suitable in the present invention, and comprises a typical batch system except that the substrate is added in increments as the culture progresses. Fed-Batch systems are useful when catabolite repression may inhibit the metabolism of the cells and when it is desirable to limit substrate in the media. Measurement of the actual substrate concentration is difficult and estimated on the basis of change in pH, dissolved oxygen and/or partial pressure of waste gases, like carbon dioxide. Batch and Fed-Batch culturing methods are well known in the art. See Thomas D. Brock, In *Biotechnology: A Textbook of Industrial Microbiology* (1989) $2^{nd}$ Ed. Sinauer Associates, Inc., Sunderland, Mass. ("Brock") or Deshpande, Mukund V. (1992) *Appl. Biochem. Biotechnol.*, 36:227-234.

Commercial production may also be accomplished with a continuous culture, which is an open system in which a defined culture medium is added continuously to a bioreactor and an equal amount of conditioned medium is removed simultaneously for processing. Continuous cultures generally maintain the cells at a constant high-liquid-phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus cell loss from drawing off the medium must be balanced against cell growth in the culture. Modulating nutrients and growth factors for continuous culture processes as well as techniques for maximizing the rate of product formation are well known in the art of industrial microbiology. See Brock, supra.

Microorganisms Having Polyester Degrading Activity

Tadros et al. (U.S. Pat. Nos. 5,990,266 and 6,191,176)) describe a mixed culture of microorganisms comprised of *Rhizopus chinensis, Rhizopus delemar, Penecillium pinophilum, Aspergillus niger*, and *Pseudomonas aeruginosa* microorganisms and their ability to degrade polyesters comprised of an amine protected glutamic acid, said polyesters having less than 60 mol percent aromatic acid content. However, 16S rRNA gene sequence analysis of the most prevalent microorganisms (based on the # of clones) in microbial culture SPDC-1 did not match any microorganisms identified by Tadros et al.

Kleeberg et al. (*Appl. Environ. Microbiol.*, 64(5):1731-1735 (1998)) identified members of a microbial consortium capable of degrading BTA co-polyesters (1,4-butanediol, adipic acid, and terephthalic acid) based on their ability to degrade the BTA co-polyesters (Poly(tetramethylene-terephtalate-co-tetramethylene-hexanedioate) having 40:60 ratio of aliphatic acid to aromatic acid content. Many of the microorganisms from the mixed culture were identified as strains of *Thermomonospora fusca*. Two of the isolates were reported to be able to depolymerize a BTA co-polyester having 60 mol percent terephthalic acid content. However, these isolates exhibited very poor growth when force to grow on BTA co-polyesters as a sole carbon source. As shown in Table 2, none of the most prevalent strains identified in microbial culture SPDC-1 were *Thermomonospora fusca*.

Wift et al. (*J. Environ. Polymer. Degrad.*, 5(2):81-89 (1997)) also reports on the ability of a consortium of microorganisms to degrade various BTA co-polyesters. Witt et al. reports that aliphatic-aromatic co-polyesters having greater than 55 mol percent terephthalic acid content do not readily biodegrade. The composition of the consortium of microorganisms was not described.

Microbial consortium SPDC-1 (ATCC PTA-6129) was developed by selecting bacteria capable of growing on a sulfonated aliphatic-aromatic co-polyester having greater than 60 mol percent aromatic acid content based on total diol or total dicarboxylic acid in the co-polyester (i.e. "Polymer B") as a sole carbon source. Additionally, the culture was supplemented with one or more of the monomers found within the polymer to enhance selection of those microorganisms capable of efficiently metabolizing the monomers released via the hydrolytic cleavage of the polymer backbone. The DNA was extracted from the consortium and 16S rRNA gene sequencing was conducted to characterize the predominant consortium members (Table 2).

A variety of microorganisms were identified from consortium SPDC-1 by comparing 16S rRNA gene sequences to publicly available sequences in GenBank®. As shown in Table 2, nearly all of the species identified had 16S rRNA genes sequences that have not been previously reported. The most predominant member of the consortium (based on the number of clones) only had 93% identity to an uncultured soil bacterium having GenBank® accession number AF507712. Microbial consortium SPDC-1 is comprised of a variety of previously uncharacterized microbial species.

The 16S rRNA gene sequences provided in Table 2 may be used to identify and/or isolate individual strains of bacteria from microbial consortium SPDC-1 using the growth conditions provided herein. One or more of the microbial species listed in Table 2 may also be used to help biodegrade sulfonated aliphatic-aromatic co-polyesters. Further, a microbial species having a 16S rRNA gene sequence selected from the group consisting of SEQ ID NOs 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, and 39 can be isolated and used to aid in the biodegradation of sulfonated aliphatic-aromatic co-polyesters having greater than 60 mol percent aromatic acid content. Isolation of the individual strains described in Table 2 can be identified and isolated from microbial consortium SPDC-1 using methods well-known in the art. See Brock, supra. The nucleic acid sequences, i.e. 16S rRNA gene sequences, described herein could be used to probe the isolated strains to identify the individual strains.

Suitable Reaction Conditions

Fermentation media in the methods described herein must contain suitable carbon substrates, which include sulfonated aliphatic-aromatic co-polyester, and monomers used to make such co-polyesters, such a terephthalic acid, adipic acid, glutaric acid, and ethylene glycol, to name a few. Suitable substrates may also include, but are not limited to, monosaccharides such as glucose and fructose, disaccharides such as lactose or sucrose, polysaccharides such as starch or cellulose or mixtures thereof and unpurified mixtures from feedstocks such as cheese whey permeate, cornsteep liquor, sugar beet molasses, barley malt, ethanol, phenol, isopropanol, and organic acids such as citrate. One of skill in the art can select the most suitable carbon source by comparing growth and activity of the microorganism(s), substrate availability, and market price of the selected carbon substrate(s).

The pH of the reactor can be from about 6.5 to about 9.5, preferably about pH 7.5 to about 8.5, more preferably about pH 8.0 (similar to pH of composting environment). The temperature of the bioreactor/composting system may range from about 45° C. to about 70° C.; or from about 50° C. to about 65° C.; or from about 55° C. to about 60° C. (similar to a composting environment).

Composting occurs optimally under aerobic conditions in a range of about 55% to about 100% relative humidity, preferably about 60% to about 100% relative humidity, more preferably about 95% to about 100% relative humidity, most preferably about 99% to about 100% relative humidity.

Suitable reaction and/or growth conditions may optionally include supplementation of the growth medium with one or more of the monomers used to create the sulfonated aliphatic-aromatic co-polyester of interest. The growth conditions may optionally include supplementation of the growth medium with a compound selected from the group consisting of terephthalic acid (and methyl esters thereof), adipic acid, glutaric acid, and ethylene glycol. The growth and/or reaction medium may comprise basal medium SMV1.

SPDC-1 may be used alone or in combination with other microorganisms either to biodegrade or to accelerate biodegradation of the sulfonated aliphatic-aromatic co-polyesters of interest in a composting system or a bioreactor. SPDC-1 can contact the sulfonated co-polyesters of interest before, during, or after such polyester is treated with an aqueous hydrolytic enzyme solution as described in International App. No. PCT/US04/16349 to Nagarajan, corresponding to U.S. patent application Ser. No. 10/852,403.

EXAMPLES

General Methods

Standard recombinant DNA and molecular cloning techniques used in the Examples are well known in the art and are described by Sambrook, J., Fritsch, E. F. and Maniatis, T. *Molecular Cloning: A Laboratory Manual*, Second Edition, Cold Spring Harbor Laboratory Press, Cold Spring Harbor (1989) (hereinafter "Maniatis"); T. J. Silhavy, M. L. Bennan, and L. W. Enquist, *Experiments with Gene Fusions*, Cold Spring Harbor Laboratory, Cold Spring Harbor, N.Y. (1984); and Ausubel, F. M. et al., *Current Protocols in Molecular Biology*, Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)), or in Brock, supra or Deshpande, supra. All reagents, restriction enzymes and materials used for the growth and maintenance of bacterial cells were obtained from Aldrich Chemicals (Milwaukee, Wis.), DIFCO Laboratories/BD Diagnostics (Sparks, Md.), Promega (Madison, Wis.), New England Biolabs (Beverly, Mass.), GIBCO/BRL Life Technologies (Carlsbad, Calif.), or Sigma Chemical Company (St. Louis, Mo.) unless otherwise specified.

The present examples illustrate the ability of microbial consortium SPDC-1 to degrade a representative sulfonated aliphatic-aromatic co-polyester (i.e. "Polymer B") having more than 60 mol percent aromatic acid content relative to the total acid content of the co-polyester. Polymer B is a sulfonated aliphatic-aromatic co-polyester comprising poly(ethylene terephthalate) with 17.5 mol percent DBE-5 (dimethyl glutarate, CAS # 1119-40-0, based on 100 mol percent total acids), 2 mol percent DRL-6 (dimethyl 5-sulfoisophthalate, sodium salt, CAS # 3965-55-7), and 8 weight. percent poly (ethylene glycol), (1000 MW, bop).

Example 1

Fed-Batch Bioreactors for Biodegradation of an Aliphatic-Aromatic Co-Polyester

Example 1 demonstrates enrichment, cultivation and maintenance of a bacterial consortium that degrades an aliphatic-aromatic copolyester in a fed-batch bioreactor. Two fed-batch bioreactors were used to enrich for bacteria that degrade the aliphatic-aromatic polyester. The first bioreactor was inoculated with compost. Biomass from the first bioreactor was then used to inoculate the second bioreactor. Analysis of the particle size distribution of the powdered aliphatic-aromatic polyester (Polymer B) indicated that the aliphatic-aromatic polyester underwent biodegradation.

The fed-batch bioreactors were composed of a 1-L dished bottom reactor (Applikon Part# Z61101C004) and controller units. A stirrer unit and controller (Applikon Part # Z5100002M0 and Controller ADI 1032 P100, part # Z510320010) were used to control mixing in the bioreactors. The stirrer had marine impellors at the bottom (Applikon part # Z81314RC03) and turbine impellors in the middle (Applikon part# Z81313R602). Bio Controller ADI 1030 Z510300020 and a pH sensor (Applikon Part # Z71201AP10) were used to control pH. A pump (Cole Parmer Pump Part # 7543-30 and pump head part # 7518-10) was used for addition of acid and base to maintain pH 8.0. The pH can vary from 6.5 to 8.5. Probes were connected to the same controller to monitor dissolved oxygen (Applikon part # Z71202AP10) and temperature (Applikon part # Z71204T002). Circulating water baths were used to pass water through the bioreactor jackets to maintain a constant temperature inside the bioreactors. Air was bubbled through the bioreactor culture medium at a flow rate of 50 mL/min since composting occurs in aerobic conditions.

The basal medium for the bioreactors was SMV1 (0.05 M potassium phosphate buffer (pH 8.0), 0.01 M ammonium sulfate, 0.001% yeast extract, 0.5 mL/L vitamin mix, (Sigma catalog # B6891 BME vitamins with 10 g per 100 mL of B12 and p-aminobenzoic acid), and metal mix consisting of the following trace metals: 2 mM $MgCl_2$, 0.7 mM $CaCl_2$, 0.05 mM $MnCl_2$, 0.001 mM $ZnCl_2$, 0.002 mM thiamine hydrochloride, 1.72 µM $CuSO_4$, 2.53 µM $CoCl_2$, and 2.42 µM $NaMoO_2$). The bioreactors were supplemented initially with 0.4% (weight/volume) powdered aliphatic-aromatic polyester (Polymer B).

Samples were routinely removed from the bioreactors and analyzed for monomers comprising the aliphatic-aromatic polyester and for the size distribution of aliphatic-aromatic polyester particles. TPA (terephthalic acid) and glutaric acid were analyzed by ion chromatography using an DIONEX (Marlton, N.J.) DX500 chromatograph with an AS3500 autosampler, ASII-HC separation column, AGII-HC guard column and Peaknet software. Samples (25 µL injection volume) were analyzed using a KOH gradient (0.5 mN to 50) with flow rate of 1.5 ml/min, SRS current of 300 mA and cell temperature of 35° C. Ethylene glycol was analyzed by gas chromatography using a HP6890 GC (Hewlett Packard) with a flame ionization detector and a DB-WAX column (30 m×0.53 mm×1 µm; Agilent Technologies, Wilmington, Del.). Samples were analyzed using helium at a column flow rate of 5 mL/min. Oven conditions for analysis were 120° C. for 1 min, ramp to 200° C. at 10° C./min and hold at 200° C. for 3 min. The particle size distribution of the aliphatic-aromatic polyester particles was measured by laser diffraction using a Beckman Coulter LS230. The samples were sonicated for 2 minutes prior to analysis.

Bioreactor BF2 was inoculated with "compost tea" and operated at 55° C. Mature compost that had been formed by mixing the sulfonated aliphatic-aromatic polyester (Polymer B) with yard compost was used to make compost tea. Compost tea was prepared from by suspending 50 g of the mature compost in 400 mL of SMV1 that was divided equally between two 1-L Erlenmeyer flasks. Both flasks were incubated at 55° C. with shaking for 48 hours. The particulate matter was then allowed to settle by incubating the flasks without shaking. The top portions of the supernatants (i.e., the compost tea) were combined, and 350 mL of compost tea was mixed with 650 mL SMV1 in the bioreactor vessel on day 0. Powdered sulfonated aliphatic-aromatic polyester (0.4% weight/volume; Polymer B) was added to the bioreactor. The bioreactor was supplemented 2 to 3 times a week with 500 mg/L TPA, 105 mg/L glutaric acid, and 228 mg/L ethylene glycol. After 75 days of operation, 100 to 200 mL of culture was removed from the reactor every 12 to 15 days. The culture sample was centrifuged, the pellet was resuspended in the original volume of fresh medium, and the resuspended cells were returned to the bioreactor. Starting on Day 90, additional amounts of TPA, sodium succinate, sodium pyruvate, ethylene glycol, and glutaric acid were added to the bioreactor at various times for degradation studies.

After 189 days of operation, all of the biomass in Bioreactor BF2 was used to inoculate Bioreactor BF4. The Bioreactor BF2 culture (940 mL) was centrifuged, and the pellet was resuspended in 1 L SMV1. Bioreactor BF4 was operated at 58° C. and was initially supplemented with 0.4% (weight/volume) powdered sulfonated aliphatic-aromatic co-polyester and monomer mix (500 mg/L TPA, 105 mg/L glutaric acid, and 228 mg/L ethylene glycol). The monomer mix was added to the bioreactor every Monday and Friday. In addition, TPA, ethylene glycol, and glutaric acid were added to the bioreactor at various times for degradation studies.

Samples were withdrawn from Bioreactor BF4 to determine the size distribution of sulfonated aliphatic-aromatic co-polyester particles using a laser diffraction technique. The sizes of the aliphatic-aromatic co-polyester particles were plotted in a volume weighted distribution that emphasized the presence of larger particles, particularly those that were greater than 40 µm in diameter (FIG. 1). The lower limit for measurement of particle diameter distribution was about 5 µm, which was approximately the size of the largest bacteria in the bioreactor. The sample of powdered sulfonated aliphatic-aromatic co-polyester that was used for this example had a broad distribution of particle diameters that ranged from less than 1 µm to about 600 µm (FIG. 1, Day 0). After 92 days, the distribution of particle volumes had shifted toward particles with smaller diameters, and none of the particles were greater than 300 µm in diameter (FIG. 1, Day 92). After 124 days, all of the particles were less than 5 µm (FIG. 1, Day 124). The reduction in particle size distribution of sulfonated aliphatic-aromatic co-polyester particles clearly demonstrated degradation of the sulfonated aliphatic-aromatic co-polyester in Bioreactor BF4.

The ability of Bioreactor BF4 to degrade terephthalic acid, glutaric acid, and ethylene glycol was tested by spiking each of these monomers individually into the bioreactor. The $O_2$ utilization rate increased in response to addition of the monomers (data not shown). Furthermore, direct analysis for the monomers indicated that the monomers were rapidly degraded (Table 1). Hence, Bioreactor BF4 was able to degrade the sulfonated aliphatic-aromatic co-polyester and the primary monomers of the polyester.

TABLE 1

Rate of Degradation for monomers comprising the sulfonated aliphatic-aromatic polyester

| Monomer | Degradation Rate (ppm/min/$OD_{600}$) |
|---|---|
| TPA | 0.169 |
| Glutaric acid | 0.179 |
| Ethylene glycol | 0.085 |

Example 2

Characterization of the Bacterial Consortium in a Fed-Batch Bioreactor for Degradation of a Sulfonated Aliphatic-Aromatic Co-Polyester Example 2 demonstrates the types of bacteria that are contained in a bacterial consortium that was maintained in a fed-batch bioreactor that was supplemented with sulfonated aliphatic-aromatic co-polyester (Polymer B). Every bacterial species has a unique 16S rRNA gene sequence. Therefore, the various types of bacteria in the fed-batch bioreactor could be identified by sequencing the products that result from using the polymerase chain reaction (PCR) to copy and amplify the different 16S rRNA genes that had been extracted from the microbial population contained in the fed-batch bioreactor. The bacterial consortium from BF4 has been deposited with ATCC and has been designated as ATCC PTA-6129.

DNA was extracted from Bioreactor BF4 biomass using a commercial kit (UltraClean Microbial Genomic DNA Isolation Kit, Mo Bio Labs, Carlsbad, Calif., part # 12224-50). The 16S rRNA genes of the bacteria in the bioreactor biomass were amplified by PCR using primers JCR14 (5'-ACGGGCGGTGTGTAC-3' (SEQ ID NO: 1) and JCR15 (5'-GCCAGCAGCCGCGGTA-3' (SEQ ID NO: 2) (5 min at 94° C. followed by 30 cycles at 94° C. for 1 min, 55° C. for 1 min, and 72° C. for 1.5 min, followed by 10 minutes at 72° C.). The PCR amplified 16S rRNA genes were purified by agarose gel electrophoresis and cloned into pCR2.1-TOTO (Invitrogen, Carlsbad, Calif.; part number K4500-01). The cloned 16S rRNA genes were sequenced using the standard M13 forward (5'-GTTTTCCCAGTCACGAC-3'; SEQ ID NO: 3) and M13 reverse (5'-CAGGAAACAGCTATGAC-3'; SEQ ID NO: 4) primers. All of the clones were initially sequenced in one direction using the M13 forward primer. Each sequence was used as the query sequence for a BLAST search (Altschul et al., *J. Mol. Biol.*, 215:403-410 (1990)) of GenBank® for the most similar previously identified 16S rRNA gene sequence. Clones that were most similar to the same GenBank® entry were grouped together.

Representatives were then selected from each group for sequencing in both directions using the M13 forward and reverse primers. Each representative sequence was used again as the query sequence for a BLAST search of GenBank® for the most similar previously identified 16S rRNA gene sequence (Table 2). Many of the species associated with the resulting GenBank® entries are recognized as thermophilic bacteria. However, only 8 of the 35 groups of cloned sequences from Bioreactor BF4 had 97% or greater identity with the corresponding most similar GenBank® sequence. Furthermore, 13 of the representative cloned sequences had less than 90% identity with the corresponding most similar GenBank® sequence. Since 16S rDNA sequences that have less than 97% identity are likely to represent different species (Stackebrandt, E. and B. M. Goebel, *Inter. J. Sys. Bacteriol.*, 44: 846-849 (1994)), these observations indicate that most of the 16S rRNA gene sequences that were derived from the biomass in bioreactor BF4 were cloned from bacteria that have not been previously isolated or characterized.

TABLE 2

GenBank ® Sequences Most Similar to 16S rRNA genes Amplified from Bioreactor BF4

| Group Identifier (16S SEQ. ID NO.) | GenBank ® Entry with Highest Identity | | | | % of |
|---|---|---|---|---|---|
| | Accession Number | Name of Organism | % Identity | No. of Clones | Total Clones |
| SPDC1-1 (SEQ. ID. NO: 5) | AF507712 | Uncultured soil bacterium | 93 | 143 | 31.1 |
| SPDC1-2 (SEQ. ID. NO: 6) | AF227859 | Bacterium | 94 | 84 | 18.3 |
| SPDC1-3 (SEQ. ID. NO: 7) | AY689031 | *Xanthomonas* sp. | 96 | 52 | 11.3 |
| SPDC1-20 (SEQ. ID. NO: 8) | X92513 | *Thermoanaerobacter wiegelii* | 88 | 27 | 5.9 |
| SPDC1-4 (SEQ. ID. NO: 9) | AF223354 | *Amycolatopsis sacchari* | 92 | 26 | 5.7 |
| SPDC1-5 (SEQ. ID. NO: 10) | AF345860 | *Rhizobiaceae* strain | 99 | 22 | 4.8 |
| SPDC1-6 (SEQ. ID. NO: 11) | AB088856 | *Pigmentiphaga* species | 99 | 21 | 4.6 |
| SPDC1-8 (SEQ. ID. NO: 12) | AJ621886 | *Desulfotomaculum geothermicum* | 89 | 12 | 2.6 |
| SPDC1-10 (SEQ. ID. NO: 13) | AY193179 | Uncultured bacterium | 87 | 8 | 1.7 |
| SPDC1-11 (SEQ. ID. NO: 14) | AY493977 | Uncultured soil bacterium | 91 | 8 | 1.7 |

TABLE 2-continued

GenBank ® Sequences Most Similar to 16S rRNA genes Amplified from Bioreactor BF4

| Group Identifier (16S SEQ. ID NO.) | Accession Number | Name of Organism | % Identity | No. of Clones | % of Total Clones |
|---|---|---|---|---|---|
| SPDC1-12 (SEQ. ID. NO: 15) | AB045091 | *Bacillus mucilaginosus* | 92 | 6 | 1.3 |
| SPDC1-13 (SEQ. ID. NO: 16) | AY117557 | *Chromobacterium violaceum* | 89 | 6 | 1.3 |
| SPDC1-18 (SEQ. ID. NO: 17) | AY499905 | Uncultured *Hyphomicrobium* sp. | 96 | 6 | 1.3 |
| SPDC1-14 (SEQ. ID. NO: 18) | AY154482 | Uncultured earthworm intenstine bacterium | 99 | 5 | 1.1 |
| SPDC1-15 (SEQ. ID. NO: 19) | AY186075 | Uncultured bacterium | 89 | 4 | 0.9 |
| SPDC1-16 (SEQ. ID. NO: 20) | AY466700 | *Anoxybacillus toebii* | 88 | 4 | 0.9 |
| SPDC1-17 (SEQ. ID. NO: 21) | AJ420142 | *Sphaerobacter thermophilus* | 99 | 3 | 0.7 |
| SPDC1-19 (SEQ. ID. NO: 22) | AY397772 | *Paenibacillus* species | 94 | 2 | 0.4 |
| SPDC1-23 (SEQ. ID. NO: 23) | AF071858 | *Bacillus* sp. | 97 | 2 | 0.4 |
| SPDC1-31 (SEQ. ID. NO: 24) | Y11567 | *Desulfotomaculum geothermicum* | 88 | 2 | 0.4 |
| SPDC1-35 (SEQ. ID. NO: 25) | AY689031 | *Xanthomonas* sp. | 93 | 2 | 0.4 |
| SPDC1-22 (SEQ. ID. NO: 26) | AB111936 | *Bacillus horti* | 91 | 1 | 0.2 |
| SPDC1-24 (SEQ. ID. NO: 27) | AF394170 | Blackwater bioreactor bacterium | 99 | 1 | 0.2 |
| SPDC1-25 (SEQ. ID. NO: 28) | AJ586382 | *Brevibacillus borstelensis* | 99 | 1 | 0.2 |
| SPDC1-26 (SEQ. ID. NO: 29) | AF174484 | *Carboxydobrachium pacificus* | 89 | 1 | 0.2 |
| SPDC1-29 (SEQ. ID. NO: 30) | AY737507 | *Geobacter hephaestius* | 86 | 1 | 0.2 |
| SPDC1-30 (SEQ. ID. NO: 31) | AB042060 | *Bacillus schlegelii* | 89 | 1 | 0.2 |
| SPDC1-32 (SEQ. ID. NO: 32) | X97690 | *Pedomicrobium ferrugineum* | 91 | 1 | 0.2 |
| SPDC1-33 (SEQ. ID. NO: 33) | AY444555 | *Photorhabdus luminescens* | 100 | 1 | 0.2 |
| SPDC1-34 (SEQ. ID. NO: 34) | AY278483 | *Thermoanaerobacter keratinophilus* | 86 | 1 | 0.2 |
| SPDC1-37 (SEQ. ID. NO: 35) | AY563464 | Uncultured bacterium | 96 | 1 | 0.2 |
| SPDC1-38 (SEQ. ID. NO: 36) | AJ308598 | *Georgenia* sp. | 92 | 1 | 0.2 |
| SPDC1-41 (SEQ. ID. NO: 37) | AF309817 | Uncultured synthetic wastewater bacterium | 88 | 1 | 0.2 |
| SPDC1-42 (SEQ. ID. NO: 38) | AY309172 | Uncultured bacterium | 87 | 1 | 0.2 |
| SPDC1-43 (SEQ. ID. NO: 39) | AB021333 | Unidentified bacterium | 91 | 1 | 0.2 |

What is claimed is:

1. An isolated bacterial consortium SPDC-1 of biologically pure cultures, said consortium SPDC-1 having ATCC accession number PTA-6129.

2. The consortium of claim 1 comprising a bacterial strain having a 16S rRNA gene sequence selected from the group consisting of SEQ ID NOs: 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39 and mixtures thereof.

3. A method of enhancing biodegradation of a sulfonated aliphatic-aromatic co-polyester having greater than 60 mol percent aromatic acid content based on total diol or total dicarboxylic acid in the co-polyester, the method comprising:

a. providing a bacterial consortium as recited in claim 1;

b. contacting the bacterial consortium with a sulfonated aliphatic-aromatic co-polyester having greater than 60 mol percent aromatic acid content based on total diol or total dicarboxylic acid in the co-polyester; and c. growing the bacterial consortium in a growth medium under suitable reaction conditions whereby the co-polyester is biodegraded.

4. The method of claim 3, wherein the bacterial consortium comprises a bacterial strain having a 16S rRNA gene sequence selected from the group consisting of SEQ ID NOs: 5, 6, 7,8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39 and mixtures thereof.

5. The method of claim 3, wherein the co-polyester comprises more than 70 mol percent aromatic acid content based on total diol or total dicarboxylic acid in the co-polyester.

6. The method according to claim 5, wherein the co-polyester comprises more than 80 mol percent aromatic acid content based on total diol or total dicarboxylic acid in the co-polyester.

7. The method according to claim 6, wherein the co-polyester comprises more than 90 mol percent aromatic acid content based on total diol or total dicarboxylic acid in the co-polyester.

8. The method of claim 3, wherein the suitable reaction conditions include a pH of from about 6.5 to about 9.5.

9. The method of claim 3, wherein the suitable reaction conditions include a temperature of from about 45° C. to about 70° C.

10. The method of claim 3, wherein the suitable reaction conditions include supplementation of the growth medium with a compound selected from the group consisting of terephthalic acid and methyl ester thereof, adipic acid, glutaric acid, ethylene glycol, basal medium SMV1 and combinations thereof.

* * * * *